US012636031B2

(12) United States Patent
   Zinnanti

(10) Patent No.: US 12,636,031 B2
(45) Date of Patent: May 26, 2026

(54) MODULAR FORCEPS

(71) Applicant: William J. Zinnanti, Santa Cruz, CA (US)

(72) Inventor: William J. Zinnanti, Santa Cruz, CA (US)

( * ) Notice: Subject to any disclaimer, the term of this patent is extended or adjusted under 35 U.S.C. 154(b) by 0 days.

(21) Appl. No.: 18/653,943

(22) Filed: May 2, 2024

(65) Prior Publication Data

US 2024/0277369 A1     Aug. 22, 2024
   US 2025/0221724 A9     Jul. 10, 2025

Related U.S. Application Data

(63) Continuation-in-part of application No. 18/205,100, filed on Jun. 2, 2023.

(60) Provisional application No. 63/348,313, filed on Jun. 2, 2022.

(51) Int. Cl.
   *A61B 17/29*     (2006.01)
   *A61B 10/06*     (2006.01)
   *A61B 17/00*     (2006.01)

(52) U.S. Cl.
   CPC .......... *A61B 17/2909* (2013.01); *A61B 10/06* (2013.01); *A61B 2017/0023* (2013.01); *A61B 2017/2925* (2013.01); *A61B 2017/2931* (2013.01); *A61B 2017/2946* (2013.01)

(58) Field of Classification Search
   CPC ..... A61B 17/2909; A61B 17/29; A61B 10/06; A61B 2017/0023; A61B 2017/2925; A61B 2017/2931; A61B 2017/2946; A61B 2017/00473
   See application file for complete search history.

(56) References Cited

U.S. PATENT DOCUMENTS

| | | | |
|---|---|---|---|
| 6,139,563 A | 10/2000 | Cosgrove, III et al. | |
| 7,771,425 B2 | 8/2010 | Dycus et al. | |
| 7,819,894 B2 | 10/2010 | Mitsuishi et al. | |
| 8,211,119 B2 | 7/2012 | Palmer et al. | |
| 11,147,613 B2 | 10/2021 | Soni | |
| 2001/0034536 A1 | 10/2001 | Looper et al. | |
| 2006/0129146 A1* | 6/2006 | Dycus ............... | A61B 18/1445 606/51 |
| 2009/0318830 A1 | 12/2009 | George et al. | |

(Continued)

FOREIGN PATENT DOCUMENTS

| | | |
|---|---|---|
| CN | 100566672 C | 12/2009 |
| WO | WO2010104755 | 9/2010 |

*Primary Examiner* — Brooke Labranche
(74) *Attorney, Agent, or Firm* — CARDINAL LAW GROUP; Douglas B Teaney

(57) ABSTRACT

A forceps system is disclosed, including a handle and a shaft-and-jaw assembly. The handle includes an immovable proximal handgrip and a lever resiliently pivotably coupled to the immovable proximal handgrip, such that exertion of a manual gripping force on the lever pivots the lever in a proximal direction toward the handgrip. The shaft-and-jaw assembly is releasably couplable to the handle, the shaft-and-jaw assembly including at least one pivotable jaw member normally biased to an open configuration, the open configuration of the jaws corresponding to a released configuration of the handle, the jaws being moved to a closed configuration upon the exertion of the manual gripping force on the lever, pivoting the lever toward the handgrip.

2 Claims, 27 Drawing Sheets

(56) References Cited

U.S. PATENT DOCUMENTS

| 2017/0273703 A1* | 9/2017 | Ding | ................. A61B 18/1445 |
| 2019/0133596 A1 | 5/2019 | Brodaczewski et al. | |

* cited by examiner

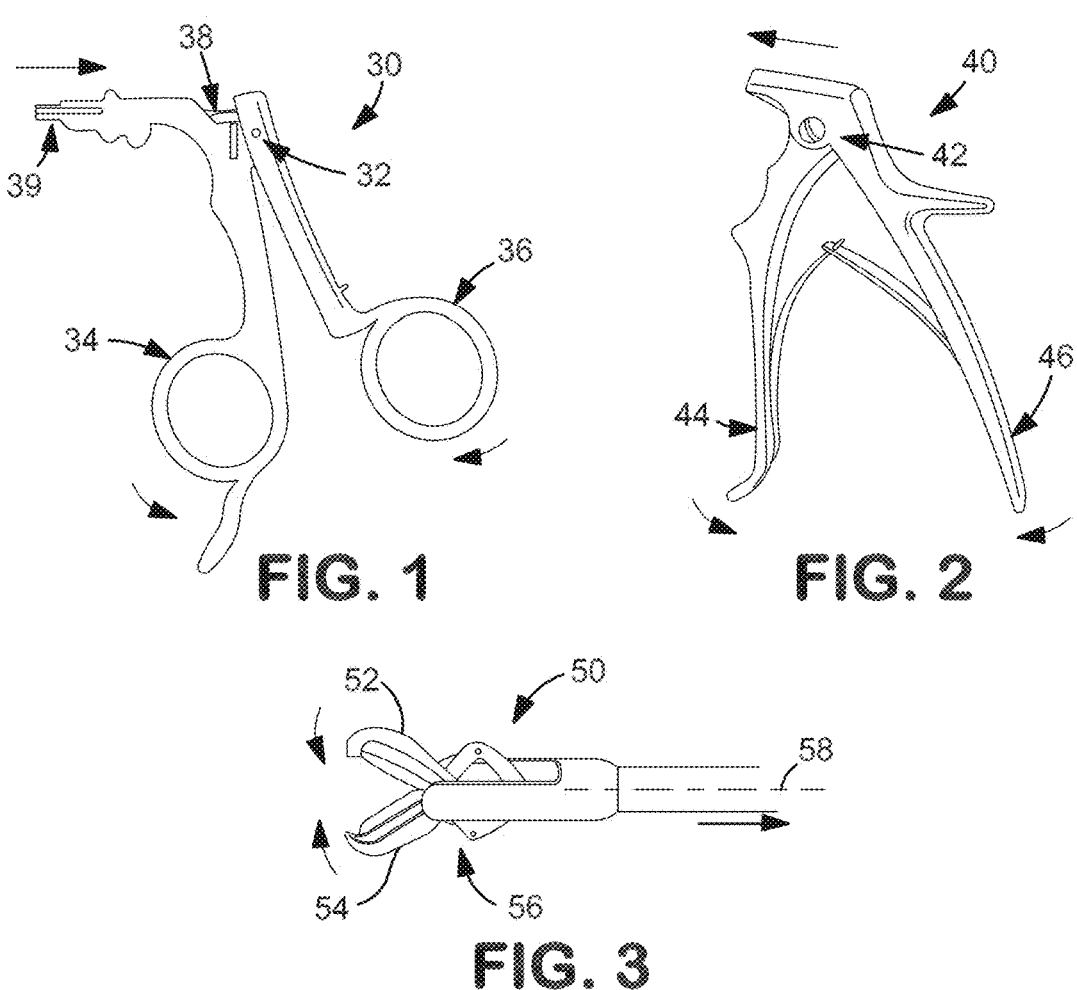
FIG. 1
FIG. 2
FIG. 3
Disposable flexible biopsy forceps passing through endoscope channel
Biopsy forceps
colonscope
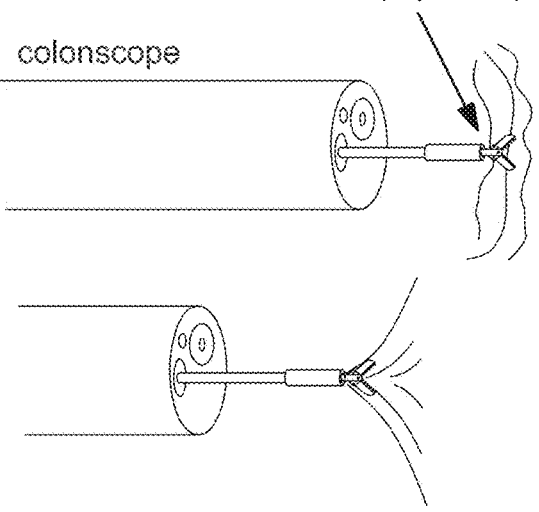
FIG. 4

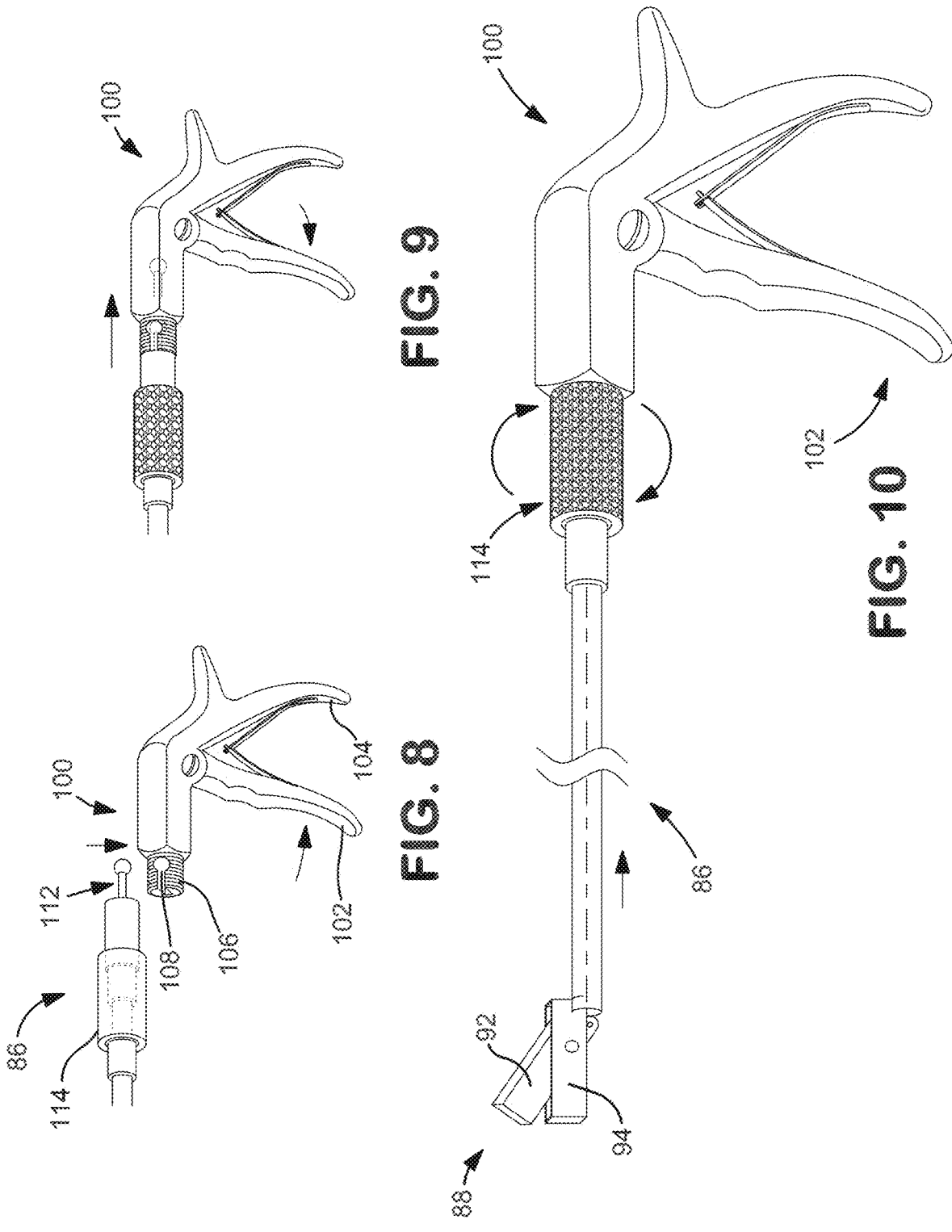

700

500

A

600

800

850

860

830

MODULAR FORCEPS

PRIORITY CLAIM

The present application claims priority under 35 U.S.C. § 120 of the filing date of U.S. Ser. No. 18/205,100, filed 2 Jun. 2023, which, in turn, claims priority under 35 U.S.C. § 119(e) of U.S. 63/348,313, filed 2 Jun. 2022, the complete contents and disclosures of both of which are hereby expressly incorporated herein by reference.

TECHNICAL FIELD

The invention relates to forceps used for medical surgical procedures.

BACKGROUND OF THE INVENTION

Biopsy is a common procedure of collecting a sample from biologic tissue to assess for the presence, cause, or extent of a disease. Tissues samples are commonly collected by forceps with sharp jaws. These forceps are used to snip off the sample from surrounding tissue. Biopsy forceps include a handle, extending shaft and collection jaws. The forceps may be reusable or disposable. Disposable forceps are preferable to provide a clean sharp set of jaws for each procedure. The extended shaft of currently available biopsy forceps is commonly ridged. Malleable versions are not detachable or single use. A ridged shaft limits access to target tissue and visualization. Therefore, biopsy forceps with a reusable handle and single use detachable malleable shaft is desirable to provide clean sharp biopsy jaws for each procedure with improved visualization and tissue access. This device can provide advantages not currently available including reduced cost and efficiency.

Biopsy of biologic tissue is a common minimal invasive procedure performed to assess tissue structure or the presence, cause, and extent of a disease. The goal of the procedure is to obtain an adequate sample while preserving the surrounding tissue. Optimum biopsies preserve the structure of the target tissue. This feature is especially important for the identification of individual layers in multilayer tissue samples. Biopsies are commonly performed with a sharp jaw forceps. The sharpness of the jaws allows for a clean cut and reduces or prevents the need to pull or tear the sample from surrounding tissue. Pulling or tearing of the tissue commonly causes more pain and bleeding during the procedure. Biopsies are often taken from tissue within a cavity. Small cavities restrict space and visualization of the tissue. Additionally, newer diagnostic modalities and equipment incorporating scopes and cameras that require direct line of site to obtain good visualization of tissues. A biopsy forceps with a malleable shaft can be bent into position and hold the position to maximize visualization and provide access to desired target tissue that may be otherwise unobtainable with a straight shaft.

Biopsy forceps with extended shafts commonly utilize an outer shaft tube and inner wire or rod mechanism to transfer mechanical force between the handle and jaws. The outer tube is fixed to the more distal portion of the handle while the inner rod is connected to the more proximal side. The two handle parts are connected at a pivot point and rotate relative to each other. The two basic designs of the handles provide a push or pull of the inner rod depending on whether the handle parts cross (FIG. 2) or not (FIG. 1) at the pivot point. Similarly, the biopsy jaw parts rotate relative to each other at a pivot point and close or open depending on whether the jaw parts cross or not at the pivot point. One common type of biopsy jaws employs a "double action" mechanism where jaws comprise four parts that cross rotate at two separate pivot points (FIG. 3). This mechanism provides symmetric action of the biopsy jaws where a pull of the inner rod causes the jaws to close. For each different design, closure of the handle provides closure of the forceps. This action is intuitive to the operator as the hand is closed to close the jaws of the forceps. Currently available biopsy forceps with an attachable detachable shaft-and-jaws are made of metal and built to withstand repeated use and sterilization. This type of sterilizable forceps employs a "push" type handle that forces the inner actuator rod forward to close the biopsy jaws. This robust construction of the shaft is too expensive for single use and cannot be made of malleable materials due to the force needed to push the distal jaws closed. Disposable forms of this biopsy forceps are made with permanently fixed plastic handles and cannot be made of malleable materials due to the required force needed to close the jaws. A second form of biopsy forceps employs a pull action to close the jaws. This shaft of this device can be made of flexible materials. The currently available devices are flexible but not malleable and will not hold a shape. This type of flexible biopsy forceps is commonly passed down a channel of a flexible endoscope (FIG. 4).

SUMMARY OF THE INVENTION

In an embodiment, disclosed are biopsy forceps with a reusable handle and attachable detachable single use shaft-and-jaws. This design utilizes a flexible internal actuator wire and a malleable outer shaft that can be bent into different shapes and hold position in the bent shape. This shaft-and-jaws can be made to be attached and detached from either push or push handle types. The shaft-and-jaws for use with a pull type handle can be made with attachment means between the outer tube to the distal portion of the handle and inner actuator rod or wire to the proximal portion. The shaft-and-jaw design for use with a push type handle requires a mechanism to convert the push force of the handle to a pull force on the inner actuator wire as the outer shaft tube is held in place. This can be accomplished by employing an attachment means between the outer shaft tube and proximal portion of the handle. The internal actuator wire can be shorter than the outer shaft tube and connect to the distal portion of the handle by a structure that slides over the outer shaft tube and connects to the inner actuating wire through an elongated opening or slot in the shaft tube. This outer structure is attached to the distal portion of the handle and provide a pull force on the internal actuating wire as it slides backwards relative to the shaft tube when the handle is closed.

An embodiment of the invention comprises a forceps system. A handle is provided, with proximal and distal handgrip sections pivotably coupled to one another at a pivot axis, a coupler structure disposed at an end of the proximal handgrip section, a biasing element mechanically disposed between the proximal and distal handgrip sections, such that proximal and distal handgrip sections are biased pivotably away from one another, the proximal handgrip section having a first end comprising a gripping portion and a second end opposite the first end comprising a coupling structure, the distal handgrip section having a first end comprising a gripping portion and a second end opposite the first end comprising a coupling structure, the pivot axis connecting the proximal and distal handgrip sections between their respective gripping portions and coupling structures, such that pivoting movement of the gripping portions of the proximal and distal handgrip sections toward one another against the biasing element corresponds to pivoting movement of the coupling structures of the proximal and distal handgrip sections away from one another. An extension has a longitudinal axis, a first end releasably couplable to the coupling structures of the proximal and distal handgrip portions, and a second end having a connector disposed thereon. An end effector is releasably couplable to the second end of the extension.

In an embodiment, the end effector including a first jaw and a second jaw, wherein at least one of the first and second jaws is pivotable about a pivot axis extending substantially perpendicular to the extension longitudinal axis. The handle, extension, and end effector in an operably coupled state, the biasing element prompting the first and second jaws toward an open configuration, the open configuration of the jaws corresponding to a released configuration of the handle, a closed configuration of the jaws corresponding to a gripped configuration of the proximal and distal handgrip portions, wherein the proximal and distal handgrip portions pivoted toward one another against the biasing element.

In an embodiment, the extension and end effector are preferably fabricated from materials which enable the extension and end effector to be fabricated in a sterile state, but which enable the extension and end effector to be at least one of discarded or recycled after use.

In an embodiment, at least one of the extension and end effector are fabricated from materials which are relatively stiff yet bendable with a modest exertion of manually-applied force, and shape-retaining once bent or formed into a desired configuration.

In an embodiment, the extension comprises a core surrounded by a sheath, the core and sheath being axially relatively movable, the core releasably couplable to the proximal handgrip portion and the sheath releasably couplable to the distal handgrip portion. In an embodiment, the coupling structure of the proximal handgrip portion comprises a hollow tubular region having an externally-threaded surface; and the core is releasably couplable to the proximal handgrip portion via an internally-threaded collar that is rotatably coupled to, but axially-fixed in relation to, the first end of the extension. In an embodiment, the core, in turn, comprises a central tension member slidably coupled relative to a surrounding tube. In an embodiment, the central tension member comprises one of a semi-rigid shaft, a wire, a braided cable.

In an embodiment, the coupling structure of the distal handgrip portion comprises a fork structure thereat, receivable within the hollow tubular region of the proximal handgrip portion, through a slot in a sidewall thereto, for arcuate reciprocating movement therein, in response to gripping and release of the handle by an operator thereof. A pin is coupled to the sheath of the extension, for axial movement therewith. A slider is axially movable within the hollow tubular region and pivotably coupled to the fork structure. The pin may have a key structure at a proximal end thereof, receivable within a corresponding key-shaped recess in a distal end of the slider, through a similar key-shaped slot a sidewall of the hollow tubular region. The key-shaped slot may be located in the externally-threaded surface of the hollow tubular region.

In an embodiment, wherein the sheath moves axially distally or proximally in response to the gripping portions of the proximal and distal handgrip sections being squeezed together or released, respectively, distal axial movement of the sheath, relative to the core, causing a pulling force to be exerted by the core on the jaws of the end effector prompting the jaws into a closed configuration.

In an embodiment, the end effector is releasably coupled to the extension.

In an embodiment of the invention, the extension is configured to be bent from an original straight configuration into a desired shape and then restored to its original configuration, through at least two cycles of bending and restoration, to facilitate multiple uses of the forceps system in multiple medical procedures. In an embodiment of the invention, the end effector is one of: permanently affixed to the extension; replaceably attachable to the extension to enable a variety of end effectors having different configurations to be employed with a single extension and handle.

In a further embodiment, a modular forceps is provided, comprising a handle assembly. The handle assembly includes a palm grip, a receiver fixedly coupled to the palm grip, and a lever, pivotably coupled to the receiver and distally positioned relative to the palm grip, the receiver defining an upwardly open slot and a distal end opening. A shaft-and-jaw assembly is releasably couplable to the handle assembly. The shaft-and-jaw assembly includes a frame having a cavity therein. An elongated hollow tube extends distally from a forward end of the frame, the hollow tube having opposed proximal and distal open ends, the hollow tube in communication with the cavity, the tube slidably received within the frame. A jaw assembly is disposed on the distal end of the hollow tube, the jaw assembly including at least a pivotable jaw pivotably mounted to the distal end of the hollow tube. An actuation member is fixedly coupled to the frame and the pivotable jaw, the tube axially movable relative to the actuation member, and an end of the lever engagable with a proximal end of the tube, such that pivoting movement of the lever toward the palm grip causes the lever to exert a pushing force on the tube, causing the distal end of the tube to, in turn, pivot the pivotable jaw from an open position to a closed position.

In this further embodiment, the modular forceps further comprises a biasing member disposed within the cavity of the frame, a distal end of the biasing member engaging an inner distal surface of the frame, a proximal end of the biasing member engaging the proximal end of the tube, such that the biasing member exerts a biasing force pushing the tube in a proximal direction relative to the frame.

In this further embodiment, the modular forceps further comprises a stop collar disposed proximate the distal end of the tube, the biasing member comprising a coil spring disposed around the distal end of the tube, a proximal end of the coil spring abutting the stop collar, a distal end of the coil spring abutting the inner distal surface of the frame.

In this further embodiment, the jaw assembly further comprises a fixed jaw fixedly coupled to the distal end of the tube, the pivotable jaw pivotably mounted to the fixed jaw.

A modular forceps system, according to this further embodiment, comprises a system, wherein at least a single handle assembly is provided and a plurality of shaft-and-jaw assemblies are provided with the handle assembly, wherein the shaft-and-jaw assemblies include one or more of a plurality of identical shaft-and-jaw assemblies having identical end effectors, a plurality of shaft-and-jaw assemblies having at least two different configurations of end effectors, a plurality of shaft-and-jaw assemblies, wherein at least one shaft-and-jaw assembly is structured to permit removal and replacement of the end effectors, with at least one of a plurality of duplicate end effectors provided and a plurality of different end effectors provided.

In an embodiment of the invention, the modular forceps further comprise an assembly lock mechanism. The assembly lock mechanism comprises at least a portion of a collar extending distally from a front region of the receiver. At least a portion of a collar extends distally from a front region of the frame. The receiver and frame collar portions at least partially mate to form a complete collar encircling a proximal portion of the hollow tube. The complete collar may be smooth, and may be engaged by a cylindrical assembly lock, through which the hollow tube passes, in an interference or friction fit. Alternatively, the receiver and frame collar portions have on an external surface thereof, threaded sections that, upon mating of the receiver and frame portions, form an at least substantially continuous external thread. In this alternative, the assembly lock cylinder is provided, through which the hollow tube is inserted, having internal threading therein, such that upon insertion of the shaft-and-jaw assembly into the receiver, the assembly lock cylinder may be reversibly and removably screwed onto the receiver and frame collar portions to maintain the shaft-and-jaw assembly securely in position in the handle assembly during use.

BRIEF DESCRIPTION OF THE DRAWINGS

FIG. 1 is a side elevation of a prior art pull-type forceps handle.

FIG. 2 is a side elevation of a prior art push-type forceps handle.

FIG. 3 is a side perspective view of a prior art pull-type double-acting jaw end effector.

FIG. 4 is an illustration of an exemplary method of use of biopsy forceps.

FIG. 8 is an illustration of a step in coupling an extension to a handle.

FIG. 9 is an illustration of a further step thereof.

FIG. 10 is an illustration of a further step thereof.

DETAILED DESCRIPTION OF THE DRAWINGS

Figure 5:
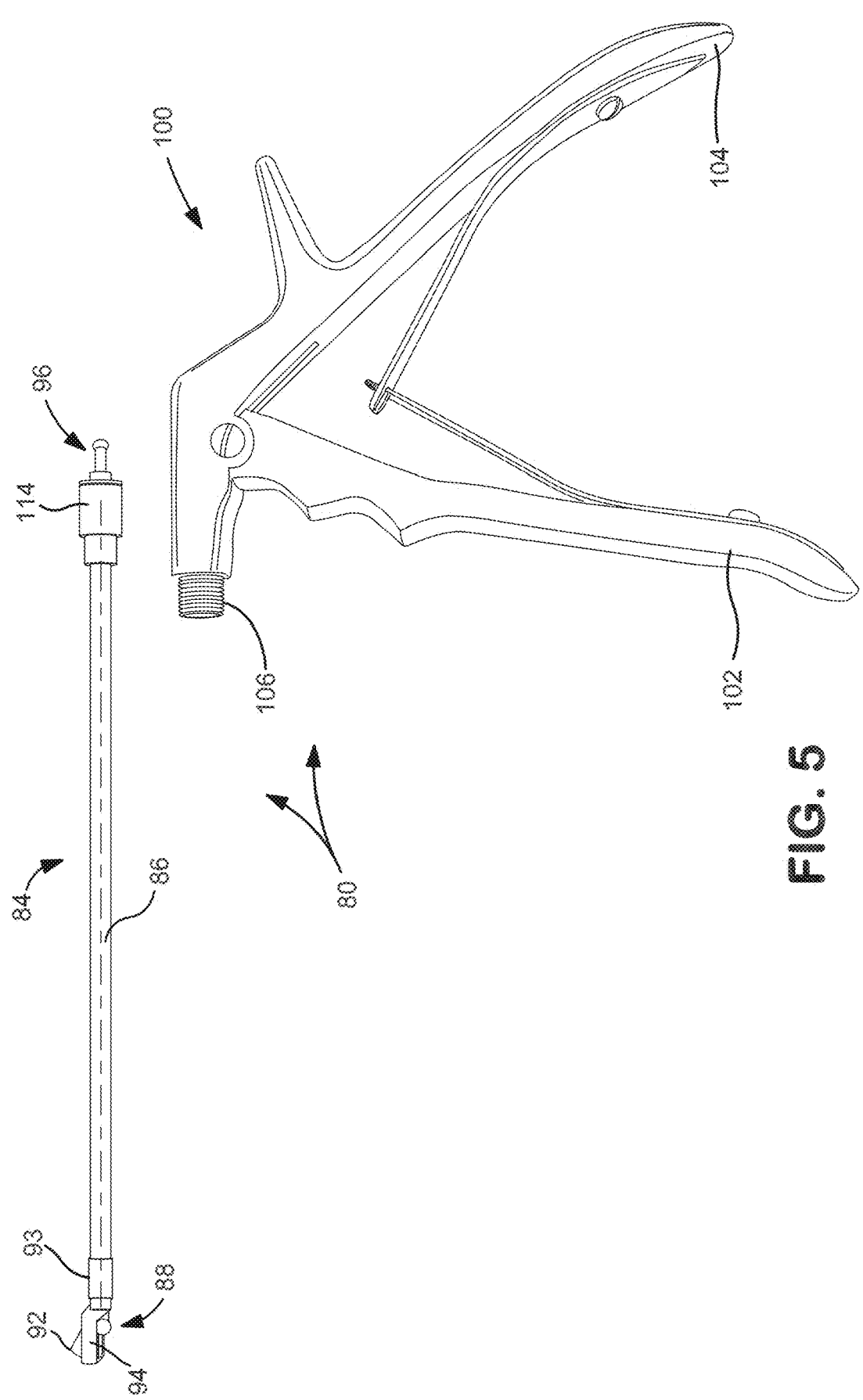
FIG. 5 is a side elevation of components of a forceps according to an embodiment of the present invention.

While this invention is susceptible of embodiment in many different forms, there are shown in the drawings and described in detail herein, specific embodiments, with the understanding that the present disclosure is to be considered as an exemplification of the principles of the invention and is not intended to limit the invention to the embodiment(s) illustrated.

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims. Unless specifically noted, it is intended that the words and phrases in the specification and the claims be given their plain, ordinary and accustomed meaning to those of ordinary skill in the applicable arts. It is noted that the inventors can be their own lexicographers. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112(f) or pre-AIA 35 U.S.C. § 112"6. Thus, the use of the words "function," "means" or "step" in the Detailed Description of the Invention or claims is not intended to somehow indicate a desire to invoke the special provisions of 35 U.S.C. § 112(f) or pre-AIA 35 U.S.C. § 112"6 to define the invention. To the contrary, if the provisions of 35 U.S.C. § 112(f) or pre-AIA 35 U.S.C. § 112"6 are sought to be invoked to define the inventions, the claims will specifically and expressly state the exact phrases "means for" or "step for" and the specific function (e.g., "means for roasting"), without also reciting in such phrases any structure, material or act in support of the function. Thus, even when the claims recite a "means for . . ." or "step for . . ." if the claims also recite any structure, material or acts in support of that means or step, or that perform the recited function, then it is the clear intention of the inventor not to invoke the provisions of 35 U.S.C. § 112(f) or pre-AIA 35 U.S.C. § 112"6. Moreover, even if the provisions of 35 U.S.C. § 112(f) or pre-AIA 35 U.S.C. § 112"6 are invoked to define the claimed inventions, it is intended that the inventions not be limited only to the specific structure, material or acts that are described in the illustrated embodiments, but in addition, include any and all structures, materials or acts that perform the claimed function as described in alternative embodiments or forms of the invention, or that are well known present or later-developed, equivalent structures, material or acts for performing the claimed function.

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and apparatus are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, apparatus and technologies to which the disclosed inventions may be applied. Thus, the full scope of the inventions is not limited to the examples that are described below.

Various aspects of the present invention may be described in terms of functional block components and various processing steps. Such functional blocks may be realized by any number of hardware or software components configured to perform the specified functions and achieve the various results.

Various representative implementations of the present invention may be applied to any system performing laparoscopic surgery. Thus, while there are disclosed improved apparatus, systems, and methods for fabrication of biopsy forceps, the principles are applicable to apparatus, systems and methods not disclosed herein. Similarly, references to methods are also applicable of systems and apparatus, which perform the processes in the operation of the recited apparatus. It will be appreciated that numerous changes may be made to the present invention without departing from the scope of the claims, including but not limited to combinations of elements or structures of the various illustrated embodiments. For example, while specific materials and/or methods of manufacture of the apparatuses described herein may be discussed, it is understood that one having ordinary skill in the art may select different materials and/or methods of manufacture, as desired or necessary to meet the requirements of a particular application, without departing from the scope of the present invention.

FIGS. 1-2 illustrate examples of known basic designs of forceps handles that provide a pull (handle 30, FIG. 1) or push force (handle 40, FIG. 2) on an inner actuating rod to open or close the biopsy jaws. In pull-type handle 30, FIG. 1, application of squeeze force to cause handle pieces 34, 36 pivot about axis 32, to move relatively toward one another, as indicated by the arrows, causing the top portion of the left (distal) handle piece 34 to move away from the right (proximal) handle piece 36, such that the top end of 36 "pulls" a central wire 38 coupled thereto, relative to an outer tube 39. In push-type handle 40 (FIG. 2), application of squeeze force causes handle pieces 44, 46 to pivot about axis 42, with the lower ends to move relatively toward one another, as indicated by the arrows, which causes the top portion of left (distal) handle piece 44, which is interior to the top of the right (proximal) handle piece and thus not visible, to move toward the left or in the distal direction relative to proximal handle piece 46, thus causing the top end of handle piece 44 to push an inner rod (not shown) towards the left, relative to proximal handle piece 46. Specifically, in such a push-type forceps, an extension (not shown) can be permanently affixed or detachably attached to the handle, and an end effector, comprising one (usually lower) jaw is fixed, and an another (usually upper) jaw, is pivotable, and the upper jaw is normally open until the handle is squeezed. The structure between the jaws and the handle comprises the extension, wherein the upper half of the extension slides, in its entirety, relative to the lower half of the extension. A tang or similar structure extends from the upper movable jaw that rides in a slot in the lower jaw, and causes the pivoting of the jaw, based on the relative movement of the upper and lower halves of the extension. In addition, due to this structure, the extension is not flexible to any meaningful degree, FIG. 3 illustrates a typical prior art biopsy jaws 50, including individual jaw pieces 52, 54, with double action scissor mechanism 56 requiring a pull (rightward arrow) of the internal actuator shaft or wire 58 (shown in broken line) for the jaw pieces to close.

FIG. 4 illustrates typical methods of use of biopsy forceps.

FIG. 5 illustrates components of a biopsy forceps 80 according to an embodiment of the invention. Forceps 80 includes handle 100 and extension 84 with shaft 86, and end effector 88, which, in FIG. 5, is illustrated as having a single moving jaw 92 and a fixed jaw 94. End effector may be permanently fixed or replaceably coupled to shaft 86, e.g., via a threaded connection between collar 93 and shaft 86. Opposite to end effector 88 is coupling 96. In a preferred embodiment of the invention, extension 84, and the components comprising extension 84 (as discussed in further detail hereinafter), are fabricated from flexible yet durable materials, which will allow the extension to be bent, as desired, and retain the shape into which the extension 84 has been formed, subject to being bent back into an original configuration. Such flexibility may be provided or enhanced by the provision of slots or gaps along the lengths of the extension (e.g., in the case of an outer tube(s)) and/or the use of flexible single-strand wire or rod, or braided wire or rope (e.g., for central members). Once assembled, tube 86, which is fixedly coupled to fixed jaw 94, is movably coupled to pin 96 and in turn, handle 102. Moving jaw 92 is, in turn coupled to internally threaded collar 114, e.g., via a stiff or semi-rigid wire or cable 97 extending along a hollow interior of shaft 86. Collar 114 and shaft 86 are in axially slidable relation to one another.

Figure 6:
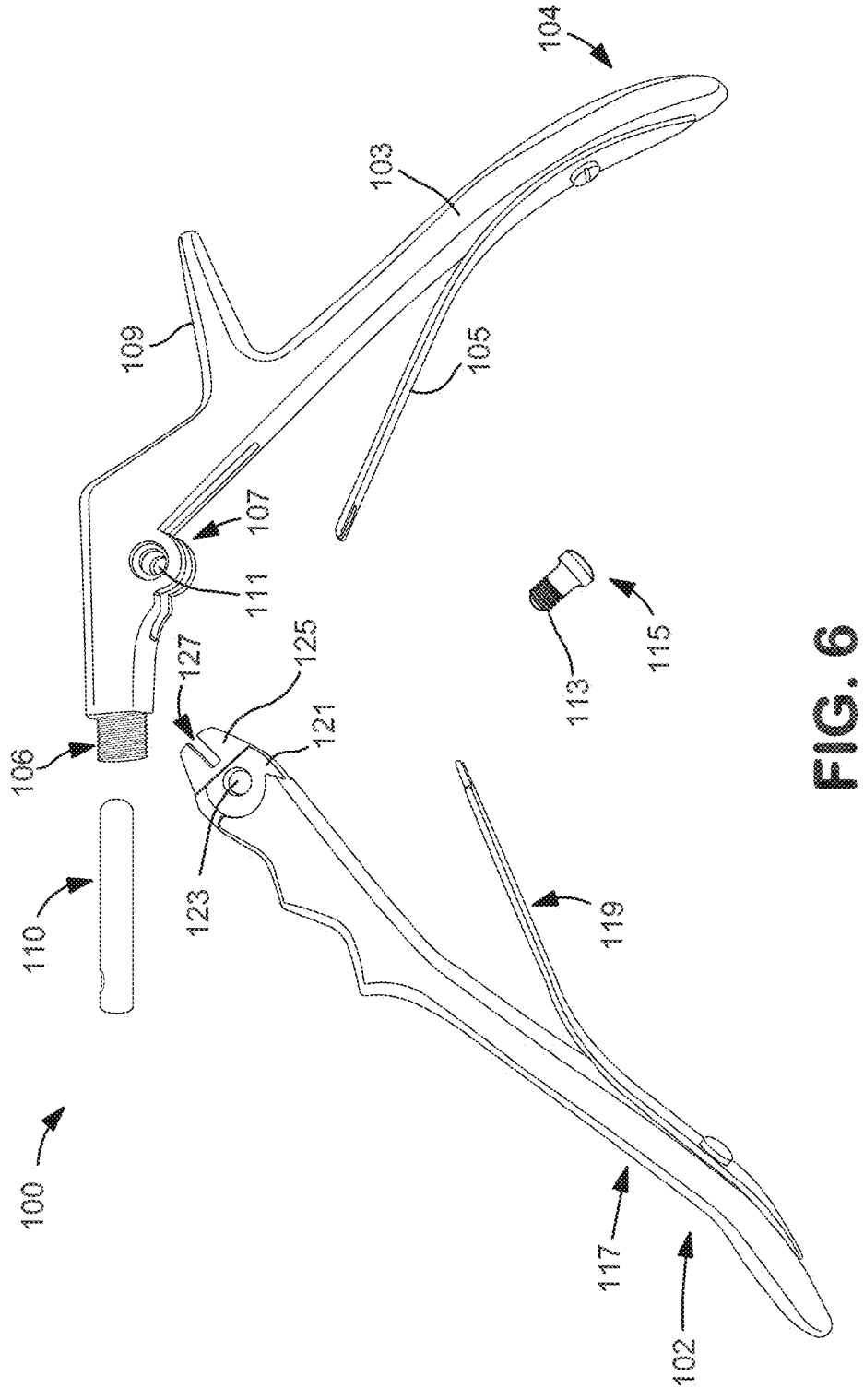
FIG. 6 is a side elevation of a handle thereof, disassembled.
Figure 7:
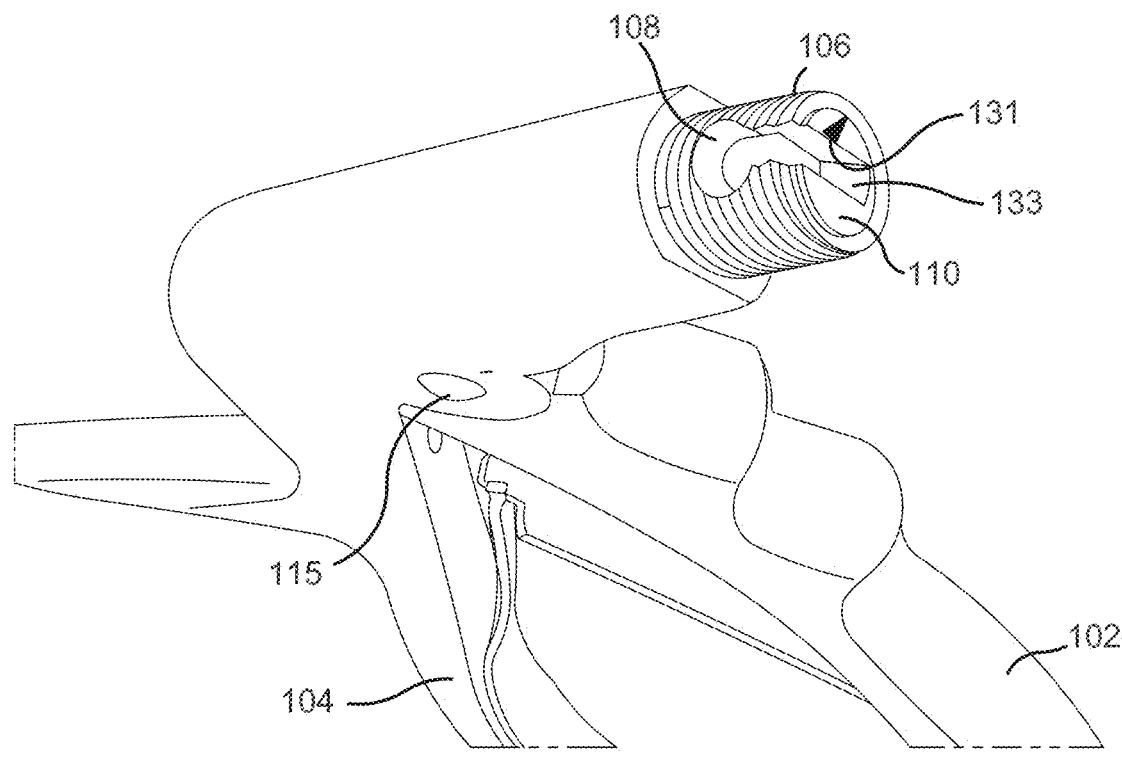
FIG. 7 is a perspective end view of the handle thereof.

FIG. 6-7 illustrate details of handle 100. Proximal grip member 104 includes palm gripping portion 103, proximal spring leaf 105 and ears 107, and thumb webbing catch 109. Spring leaf 105 may be affixed to grip member 104 by any suitable mechanism, e.g., a screw or rivet (not shown). Each ear 107 includes a through-bore 111, one of which, in an embodiment, is threaded, to receive threads 113 of fastener 115. Lever 102 includes finger grip surface 117, distal spring leaf 119, recesses 121 (one on each side of lever 102) with smooth through-bore 123, and fork 125. Spring leaf 119 may be affixed to lever 102 by any suitable mechanism, e.g., a screw or rivet (not shown). Threaded collar 106 surrounds a bore 131 (FIG. 7) which slidingly receives slider 110. Slider 110 includes a further slot 135 (shown in FIG. 29), spanned by cross-bar 137, which engages and is received within notch 127 of fork 125.

FIG. 8-10 illustrate a method for attaching extension 84 to handle 100. FIG. 8 illustrates handle 100, with movable distal lever 102 pulled back toward fixed proximal grip member 104. This compression or pulling of lever 102 causes slider 110 (FIG. 6-7) in bore at an upper end of lever 102 to move forward (to the left in FIG. 8). Handle 100 further includes an externally-threaded collar 106 having a generally keyhole shaped side slot 108. Slider 110 includes slot 133 which, when viewed from above, as a similar outline as slot 108. Accordingly, when slider 110 is in its forward position. Slots 108 and 133 align, to accommodate beaded end 112 of extension 84. Release of lever 102 (FIG. 9) causes the slider of lever 102 to move to the right, inwardly, pulling beaded end 112 with it into the interior of the handle 100 as shown in FIG. 9. Internally-threaded collar 114 is slid to the right, to engage externally-threaded collar 106, as shown in FIG. 10.

Figures 11, 12, 13:
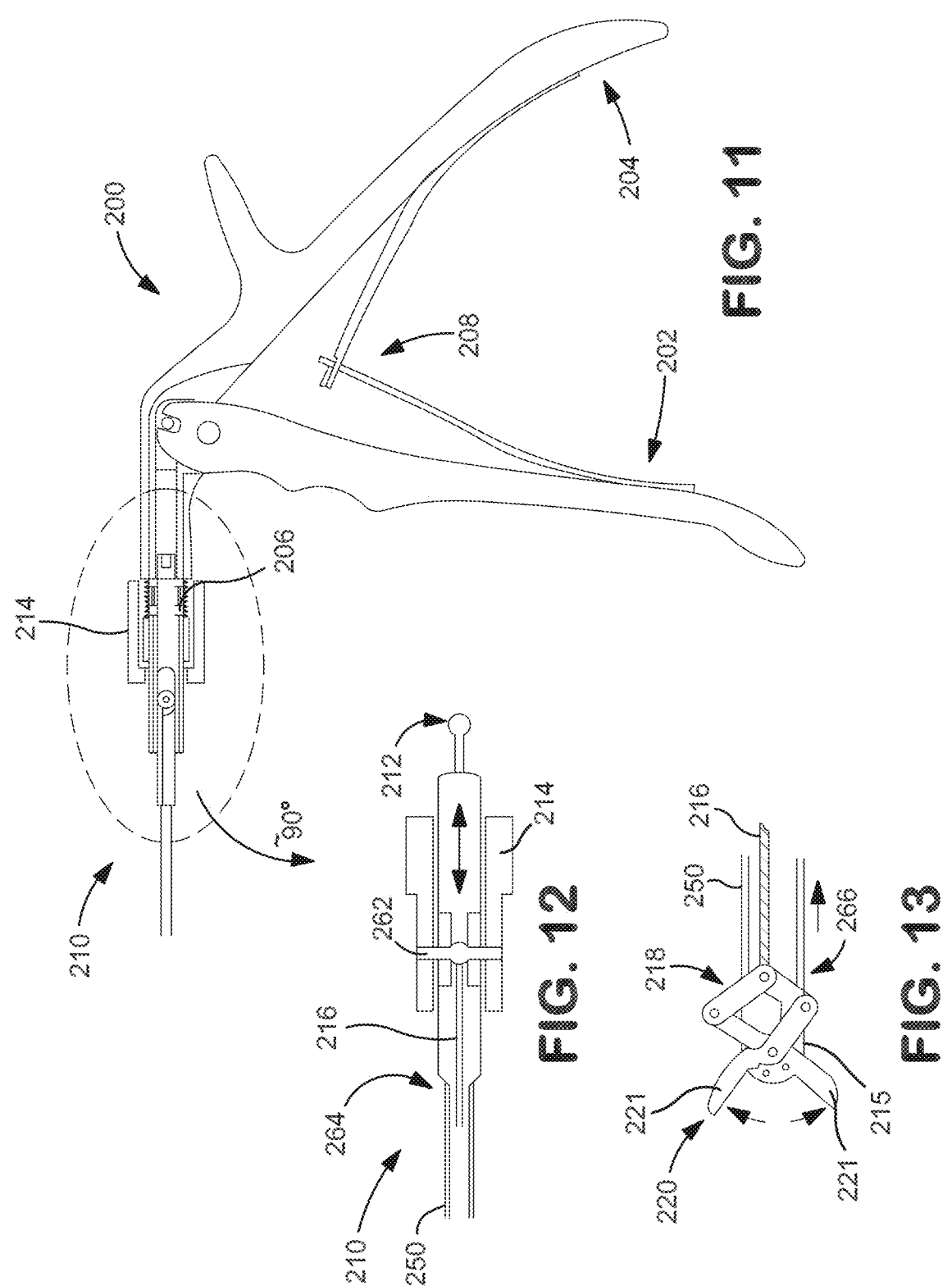
FIG. 11 is a side elevation, partly in section, of a handle coupled to an extension.
FIG. 12 is an enhanced view of a proximal end of an extension.
FIG. 13 is a sectional view of an end effector.

FIG. 11-13 illustrate, in partial side section, components of a push-type forceps, similar to the embodiment of FIG. 5-10, with the jaws in the open configuration, according to an embodiment of the invention. FIG. 11 illustrates a handle 200 together with a flexible shaft-and-jaw assembly (or extension) 210, as previously described, with internally threaded collar 214. Handle 200 includes movable lever 202, fixed grip portion 204 and threaded collar 206. FIG. 12 illustrates the proximal end of shaft-and-jaw assembly 210, with internally-threaded collar 214 omitted. FIG. 12 further illustrates the proximal portion of shaft-and-jaw assembly 210 rotated 90 degrees, relative to the side elevation of FIG. 11. Core wire or cable 216 is fixedly coupled, via pin 262, to FIG. 13 illustrates end effector 220, having jaws 221, and housing 215. In an embodiment of the invention, housing 215 is monolithically formed or permanently affixed to tube 250; in alternate embodiments, housing 215 may be releasably coupled to tube 250, with core wire or cable 216 likewise releasably coupled to the proximal portion of the scissor mechanism illustrated in FIG. 13 for jaws 221 of end effector 220. Releasing lever 202 allows handle spring arrangement 208 to move lever 202 and grip 204 apart to the released or "at rest" orientation, which, in turn, causes elongated tube 250 to move toward the right (from the perspective of FIG. 13 as indicated by the arrow). As core wire/cable 216 has some stiffness, it pushes on the proximal end link of linkage 218 to collapse linkage 218 laterally and spread "vertically" (again relative to FIG. 13), opening jaws 220.

Figures 14, 15, 16, 17:
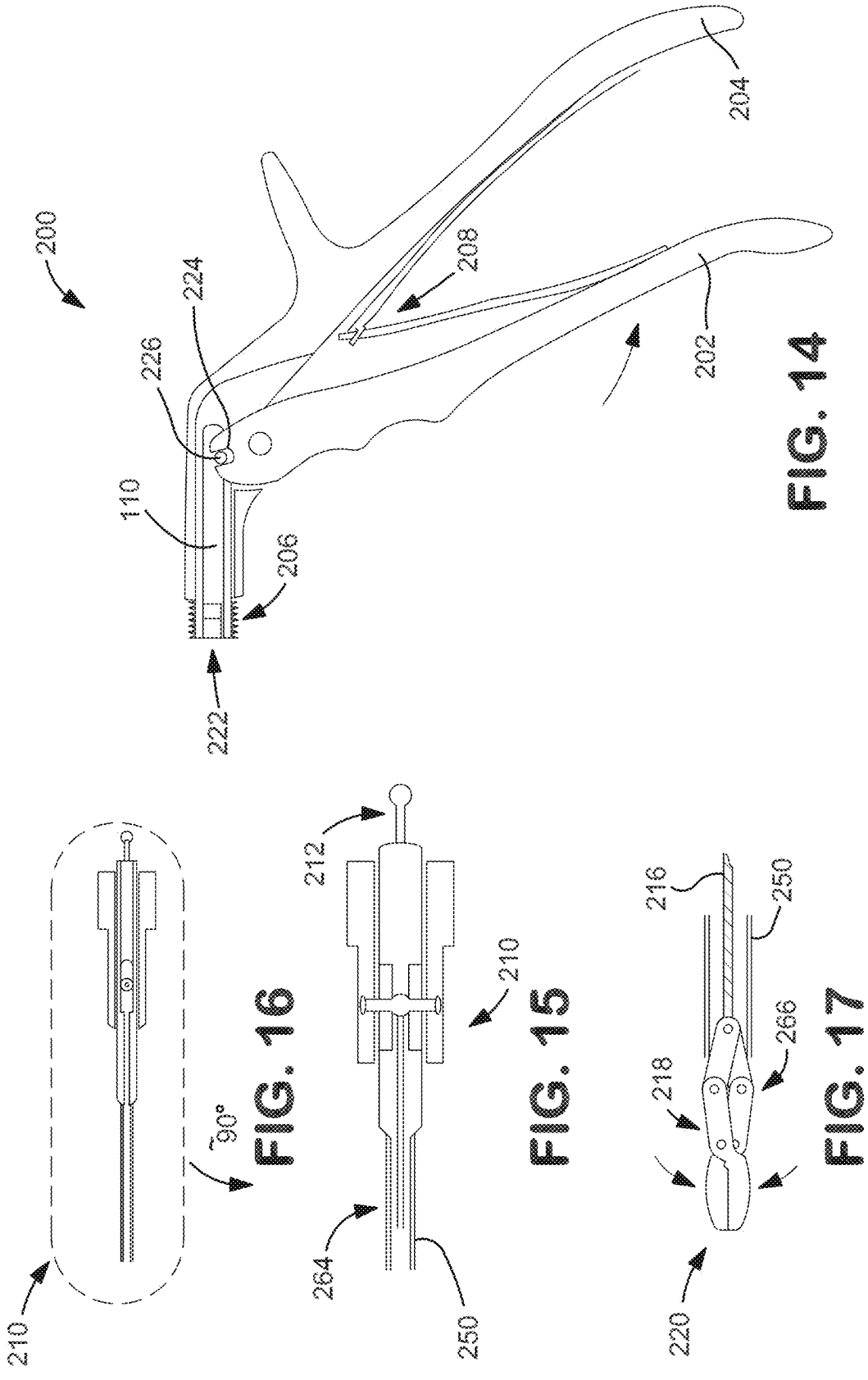
FIG. 14 is a side elevation, partly in section, of a handle in the squeezed configuration.
FIG. 15 is an enlarged sectional view of a coupling of an extension.
FIG. 16 is a view thereof, rotated 90 degrees about a longitudinal axis there.
FIG. 17 is a view of an end effector in a closed configuration.
Figure 18:
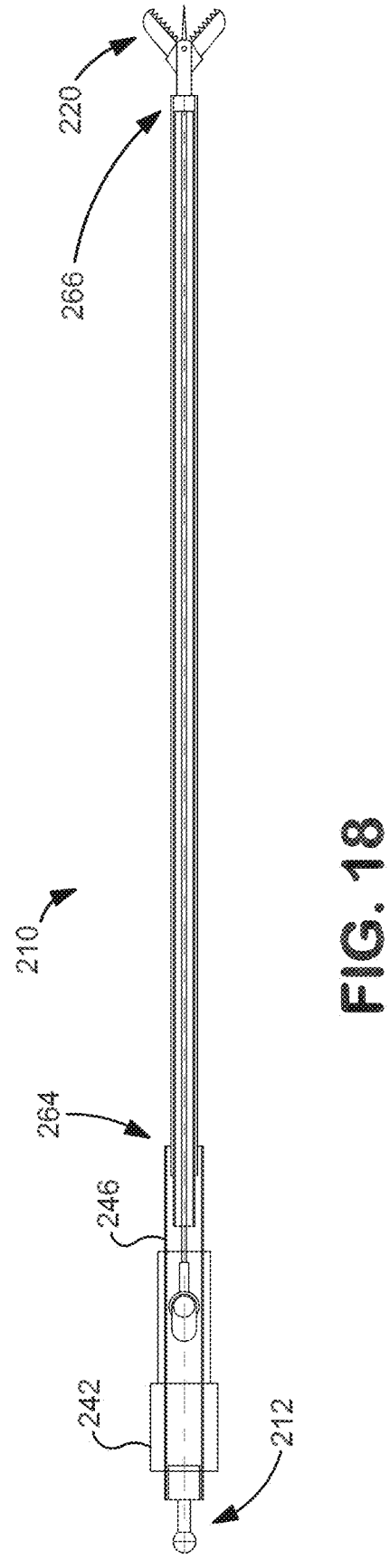
FIG. 18 is a side elevation partly in section of a core of an extension, with end effector.
Figures 19, 20, 21, 22, 23:
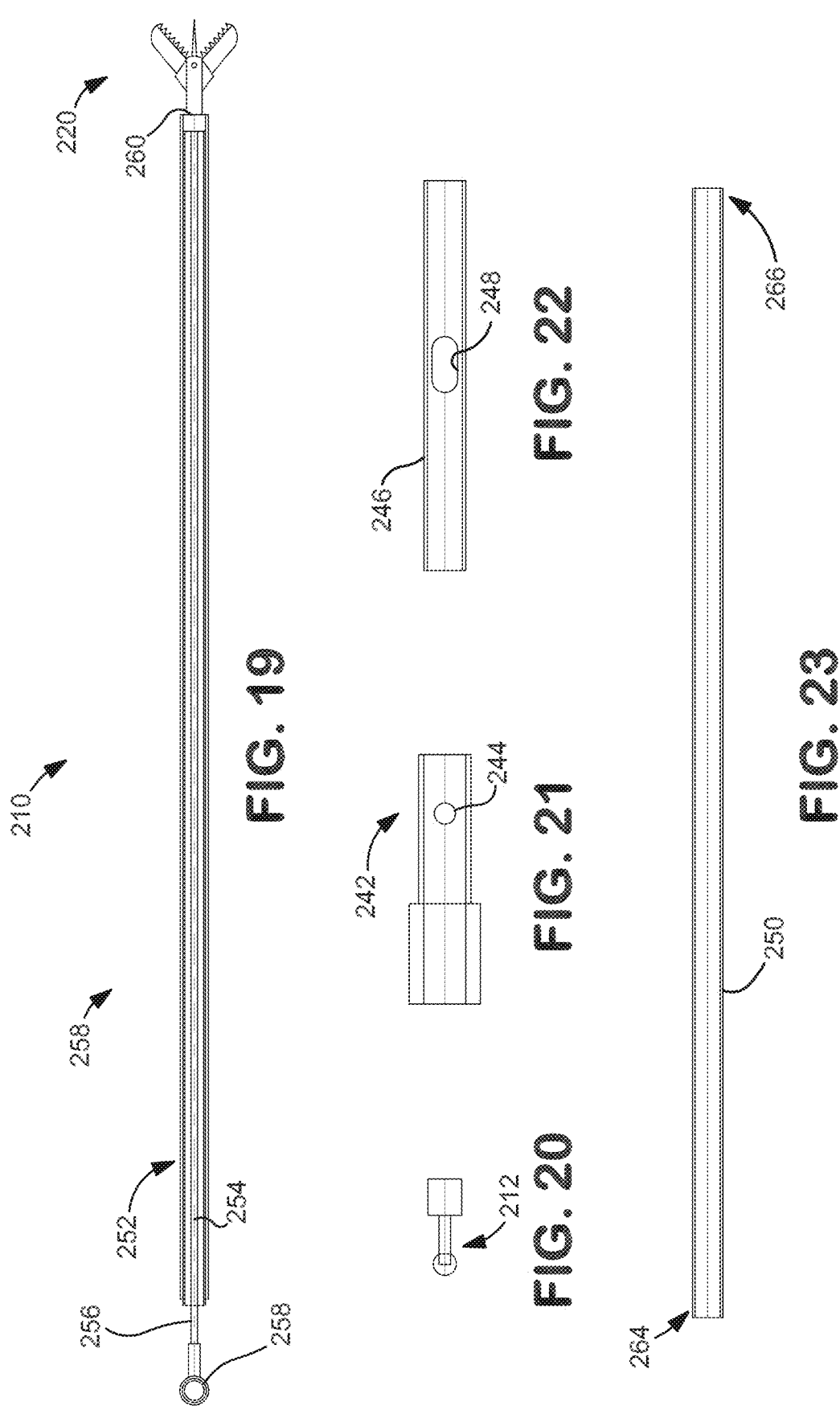
FIG. 19 is a further view thereof.
FIG. 20 is a view of a coupler pin.
FIG. 21 is a view of a threaded collar.
FIG. 22 is a view of a sliding sleeve.
FIG. 23 is a view of an outer tube of the core.

FIG. 14-17 illustrate, in partial side-section, components of the push-type forceps of FIG. 11-13, with the jaws in the closed configuration, according to an embodiment of the invention. Handle 200 includes lever 202, having a slot 224, which receives a pin 226 attached to or emanating from, a slider 110, such that when lever 202 is squeezed, slider 110 moves from right to left from the perspective of FIG. 14, moving tube 250, and in turn housing 215, to move in a distal direction, against the "pull" of static core cable 216, causing jaws 220 to close, as shown in FIG. 17. FIG. 15 illustrates the proximal portion of shaft-and-jaw assembly 210 rotated 90 degrees, relative to the side elevation of FIG. 16.

FIGS. 18-23 illustrate components for the modular flexible (and/or bendable and shape-retaining) shaft-and-jaws, similar to that shown in FIG. 11-17. shaft-and-jaw assembly 210 includes a core, comprising main body 252 which may include a braided wire 254, straight wire 256, loop 258. A plug 260 with jaws 220 extending therefrom, defines the distal end of shaft-and-jaw assembly 210. Jaws are configured for relative pivoting movement between closed (FIG. 17) and open (FIG. 13) orientations, with jaws 220 biased to an open orientation through the action of spring 208. shaft-and-jaw assembly 210 further includes bead section 212, fixed sleeve 242 having circular openings 244 on diametrically opposed sides thereof, sliding sleeve 246 having elongated openings 248 on diametrically opposed sides thereof, and elongated sliding tube 250. Sliding tube 250 includes proximal end 264 and distal end 266, as shown in FIG. 18-23, 26-27. Sliding sleeve 246 is insertably received within fixed sleeve 242 and fixedly coupled for movement with tube 250, and a proximal end of the core (210 minus plug 260 and jaws 220). Assembly 220 further includes pin 262, which passes through loop 256, elongated openings 248, and has its ends situated at or within openings 244. Further details of the interaction of pin 262 and loop 256 are discussed hereinafter with respect to FIG. 28. With respect to FIGS. 18 and 19, end 266 of tube 250 is coupled to the housing of jaws 220, for axial movement therewith. Core cable/wire 254 (shown in FIG. 19) is fixedly coupled to a proximal end of a scissor mechanism for jaws 220, and is likewise fixedly coupled to fixed sleeve 242. To complete assembly, fixed sleeve 242 is captured axially by internally threaded collar 214. In an alternative embodiment, sliding sleeve 246 and tube 250 may be fabricated as a single monolithically formed structure.

In operation, once shaft-and-jaw assembly 210 is coupled to a handle 200, in the manner described above, bead section 212 and slider 110 are locked together in simultaneous axial movement. When lever 202 and grip 204 are squeezed together, slider 110 is moved in a distal direction, together with bead section 212. Bead section 212 in turn pushes sliding sleeve 246 in a distal direction, together with elongated tube 250 and jaws 220. The distal movement of tube 250 is axially relative to core 254, which pulls on the scissor linkage for jaws 220 and causes them to close. When pressure on lever 202 is released, spring arrangement 208 pushes lever 202 toward a distal position relative to grip 204. This causes slider 110 and bead section 212 to move proximally toward grip 204. Elongated tube 250 is in turn moved proximally, in the reverse direction as previously described. Inasmuch as core cable 254, while flexible has some axial stiffness, and is of course enclosed in a narrow tube, core cable 254 will push on the linkage, collapsing it axially and causing the jaws to open. Tube 250, sliding sleeve 246 and bead section 212 may be coupled together using any suitable mechanism, such as force-fit, crimping, spot-welding, brazing, etc.

Figure 24:
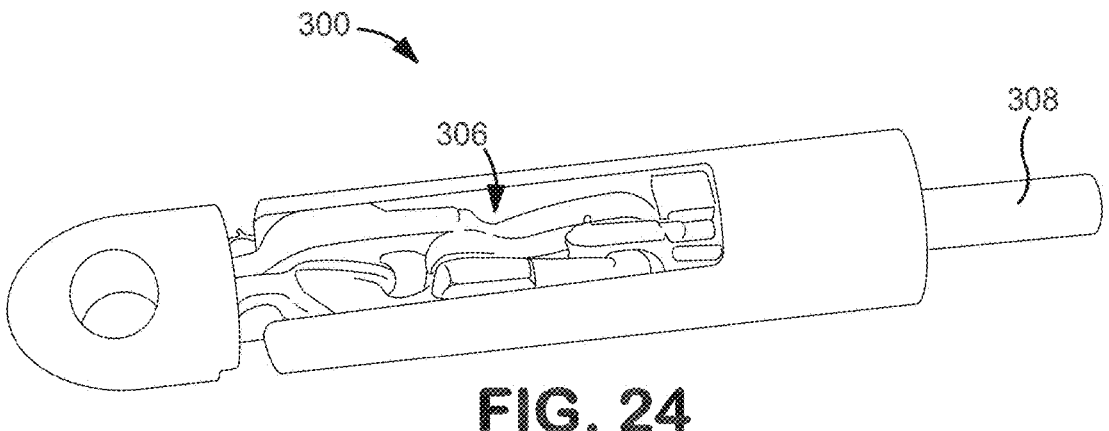
FIG. 24 is a view of an end effector in closed configuration.
Figure 25:
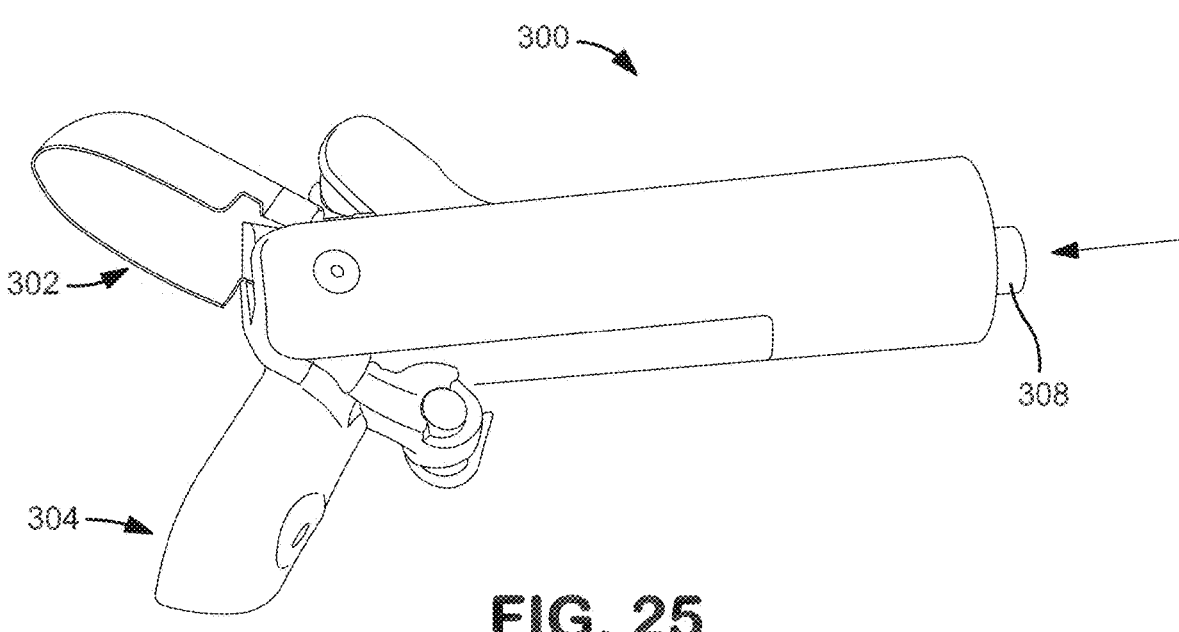
FIG. 25 is a view of an end effector in open configuration.
Figure 26:
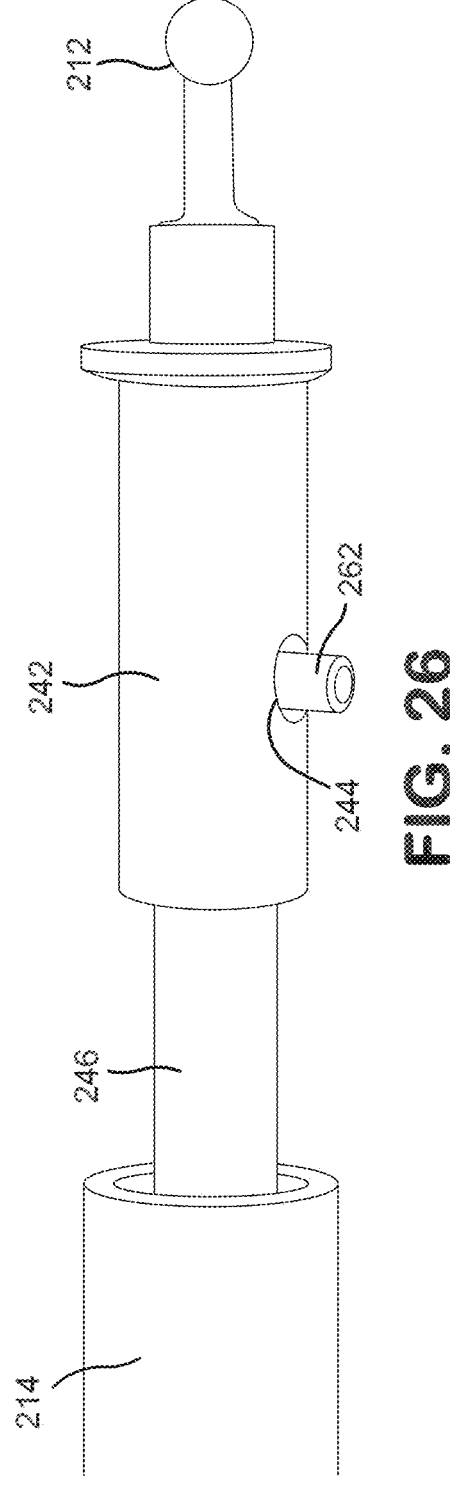
FIG. 26 is a side view of the coupling region for an extension.
Figure 27:
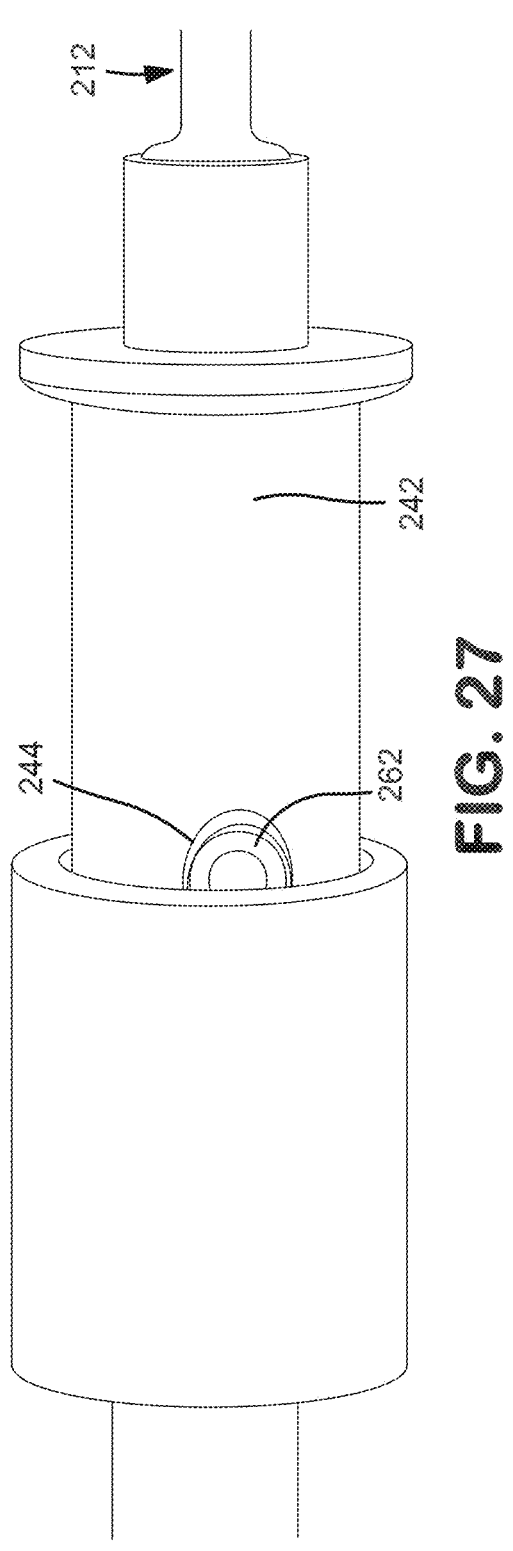
FIG. 27 is a further view thereof.

In a preferred embodiment, the components comprising shaft-and-jaw assembly 210 are fabricated from materials which are relatively stiff yet bendable with a modest exertion of manually-applied force, and shape-retaining once bent or formed into a desired configuration. Further, the components comprising handle 200 preferably are fabricated from durable, sterilizable materials, such as are known in the art, while the components comprising shaft-and-jaw assembly 210 may be fabricated either as sterilizable and reusable, or from materials which enable shaft-and-jaw assembly to be fabricated in a sterile state, but which may be readily discarded and/or recycled, FIG. 24-25 illustrate a double-action, dual jaw end effector 300 having jaws 302, 304 and a scissor mechanism 306 coupled to post 308, such that when post 308 is pushed in a distal direction (arrow), jaws 302, 304 open, and when post 308 is pulled in a proximal direction, jaws 302, 304 close. Post 308 may be couplable to a core cable or wire using any suitable mechanism, such as a threaded coupling, snap fit, hook, etc.

Figures 28, 29:
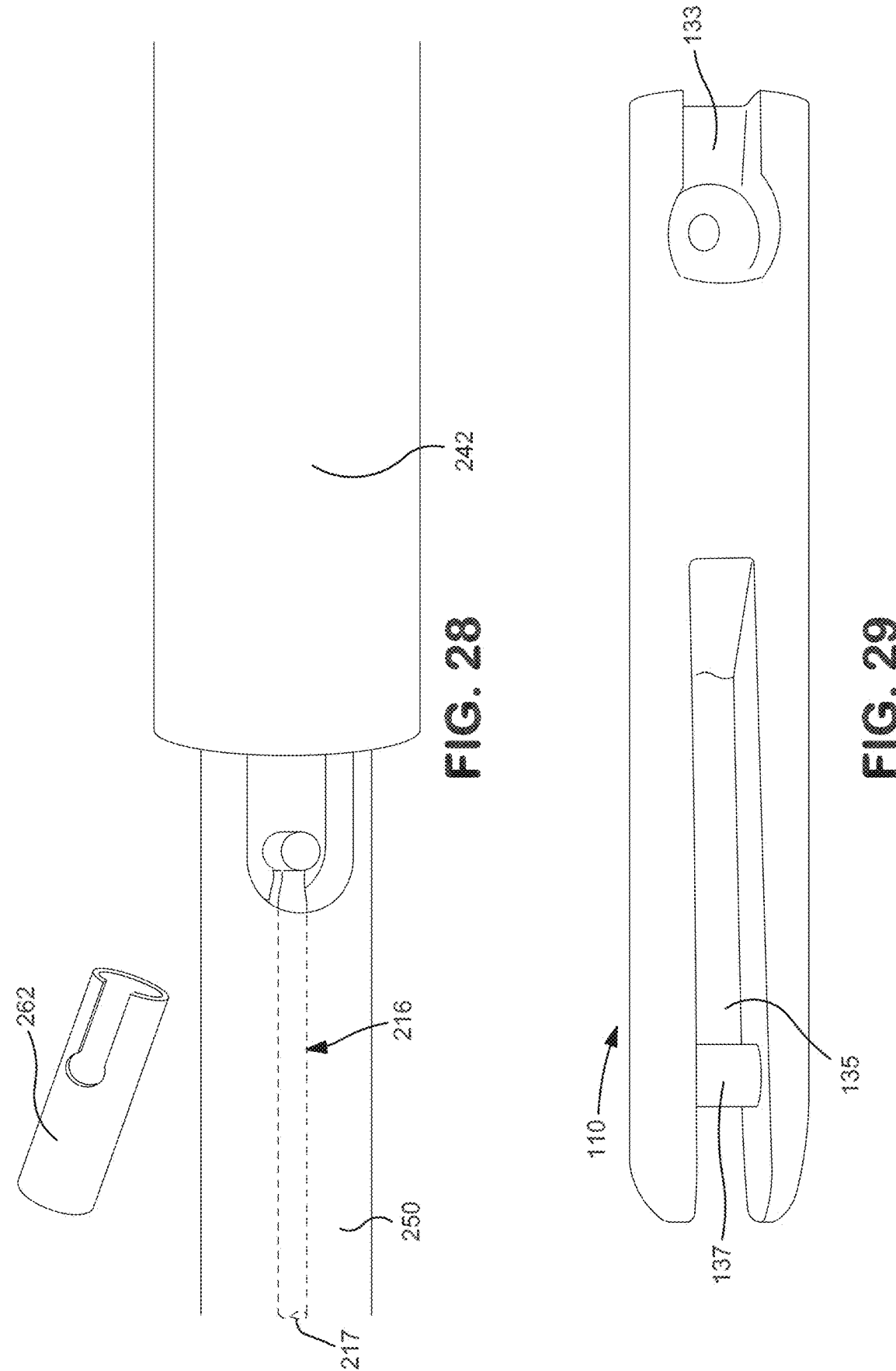
FIG. 28 is an enlarged view of the mechanism for affixing the core cable or wire to the handle housing.
FIG. 29 is a side view of a slider.

FIG. 28 is an enlarged view of fixed sleeve 242, sliding tube 250, core wire 216 (similar or identical to core cable 254 elsewhere described) having a barrel plug 217 at a proximal end thereof, and tubular pin 262, which has an axial slot therein. To assemble core wire 216 to fixed sleeve 242, core wire 216 is inserted into tube 250 until barrel plug 217 becomes aligned with the openings in fixed sleeve 242. Pin 262 is then inserted through the openings in sleeve 242 with its slot aligned with core wire 216, such that barrel plug 217 is captured in the interior of pin 262.

FIGS. 30-38 illustrate another embodiment of the present invention.

Figure 30:
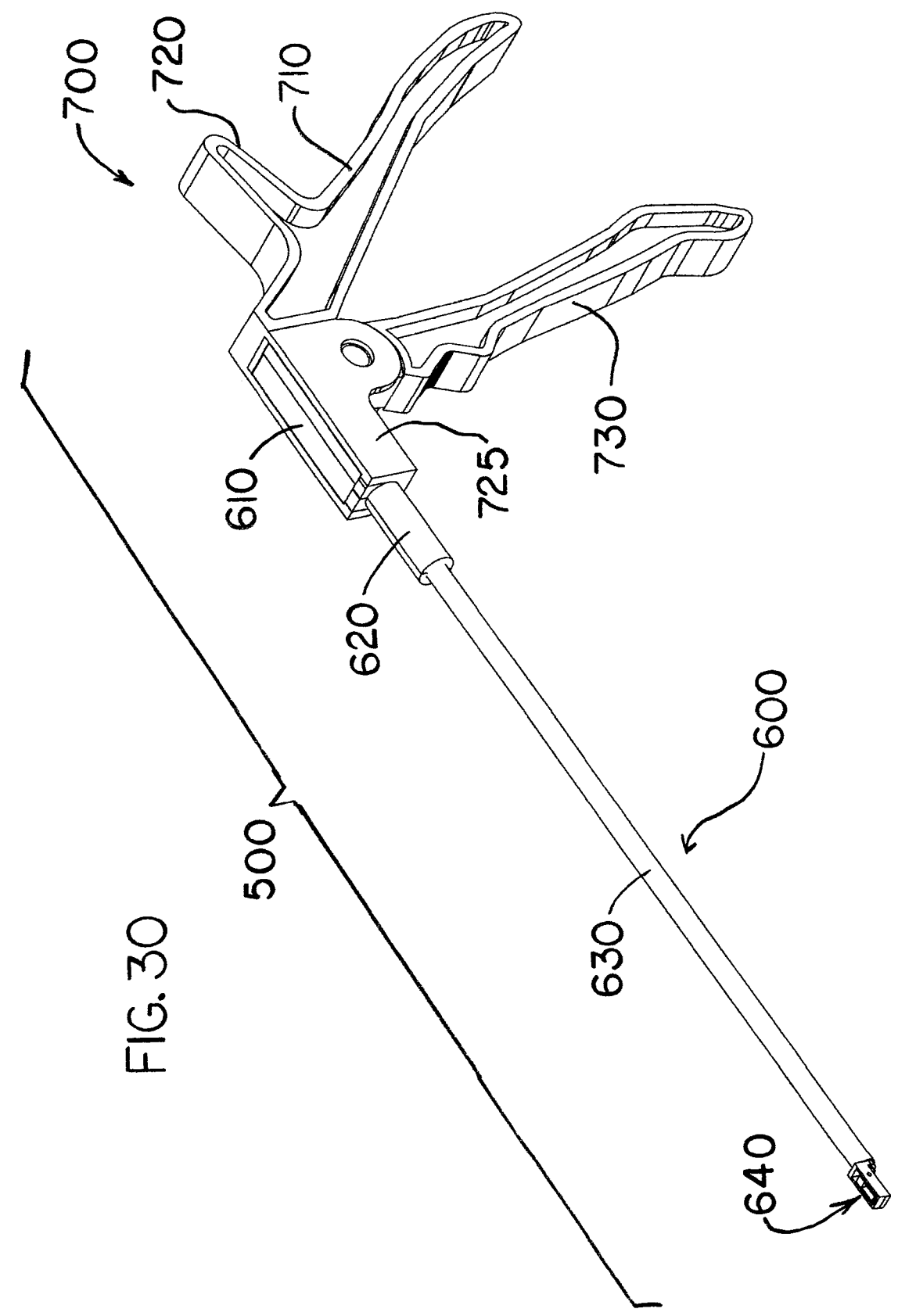
FIG. 30 is a perspective view of the invention, according to another embodiment.
Figure 31:
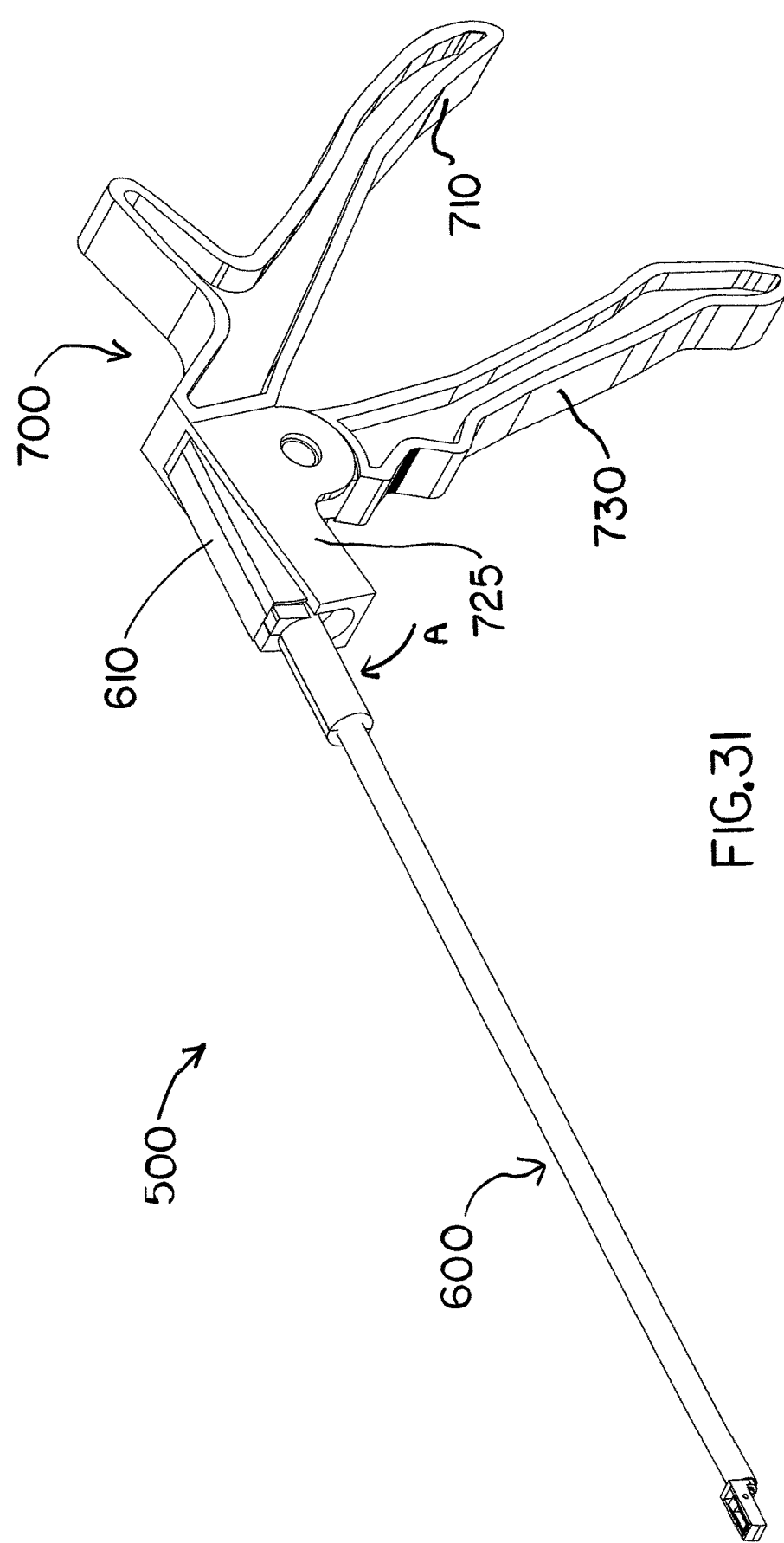
FIG. 31 is a perspective view of the forceps embodiment of FIG. 30, showing the shaft-and-jaw assembly partially removed from the handle assembly.
Figure 32:
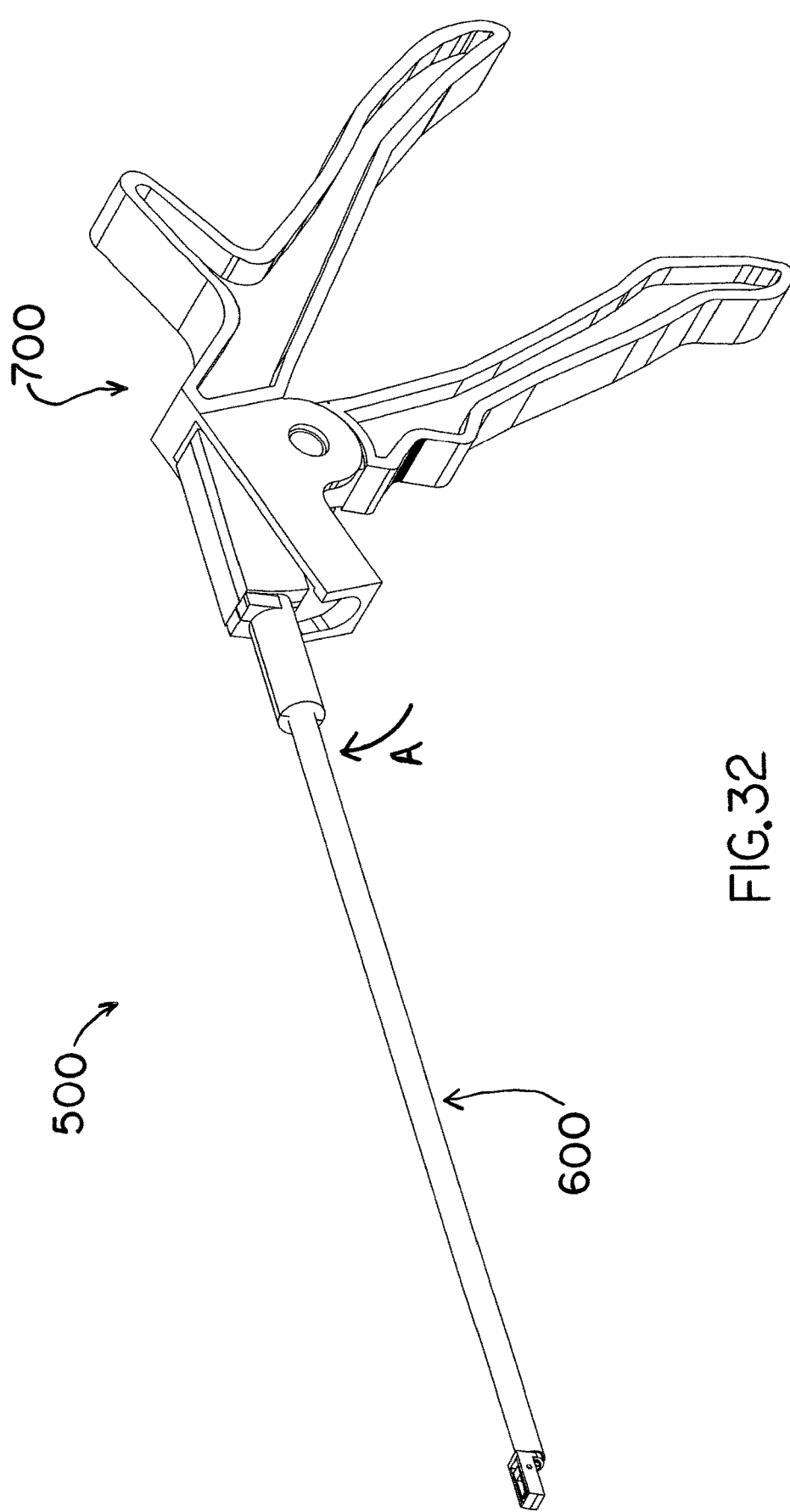
FIG. 32 is a further perspective view of the forceps embodiment of FIG. 30, showing the shaft-and-jaw assembly further pivoted relative to the handle assembly.
Figure 33:
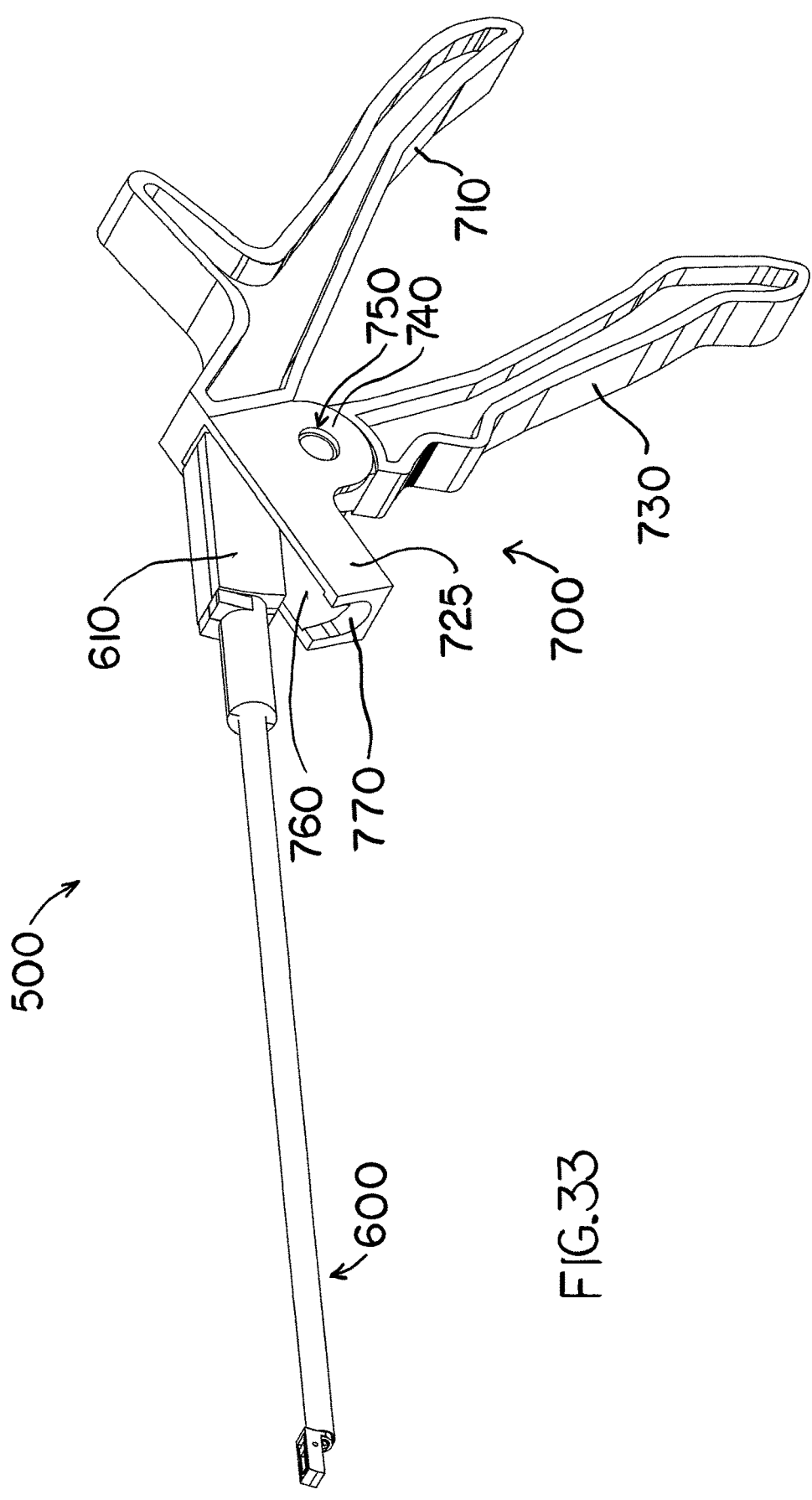
FIG. 33 is a still further perspective view of the forceps embodiment of FIG. 30, showing the shaft-and-jaw assembly further pivoted relative to the handle assembly.
Figure 34:
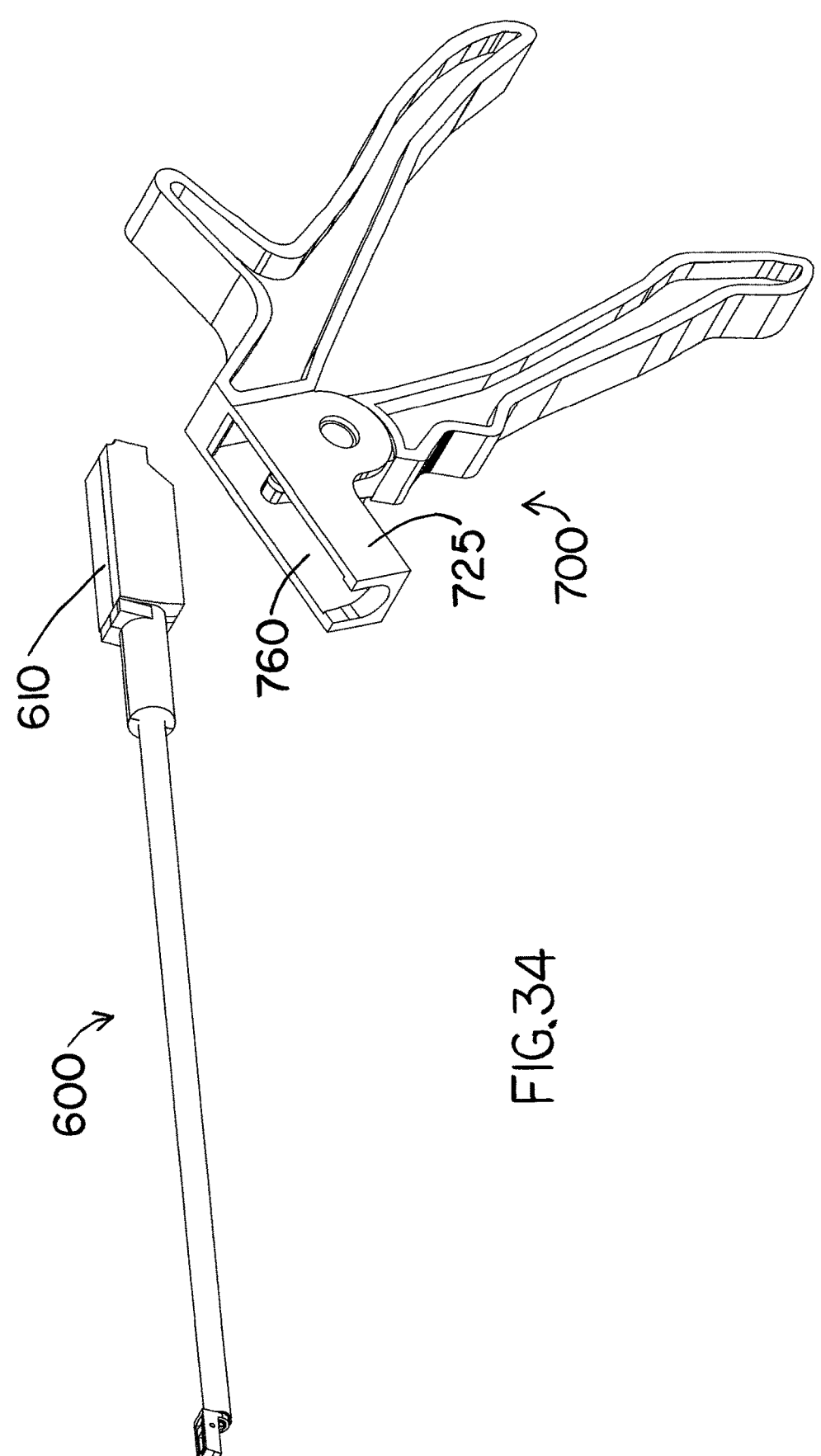
FIG. 34 is a still further perspective view of the forceps embodiment of FIG. 30, showing the shaft-and-jaw assembly fully separated from the handle assembly.

FIG. 30 is a perspective view of the invention, Modular forceps 500 comprises shaft-and-jaw assembly 600 and handle assembly 700. Shaft-and-jaw assembly 600 includes box frame 610, collar 620, tube 630 and end effector 640. Tube 630 is slidably mounted in frame 610 and collar 620. Handle assembly 700 includes palm grip 710 with spur 720, receiver 725, and lever 730. As illustrated in FIG. 33, receiver 725 defines two ears 740 (only one of which is seen in FIG. 33), each having a circular aperture 750. Receiver 725 further defines an upwardly-opening slot 760 having a U-shaped distal end opening 770.

Figure 37:
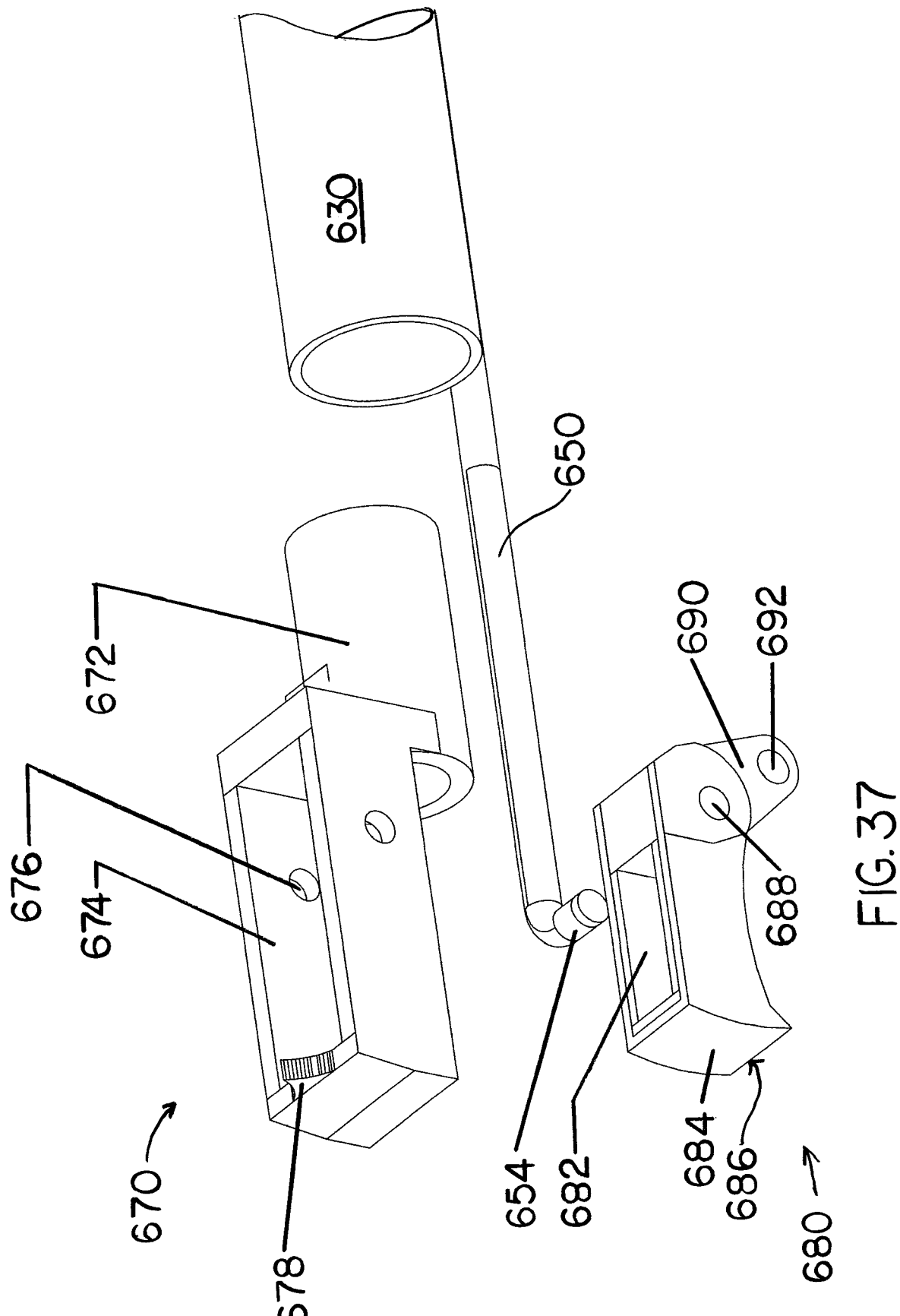
FIG. 37 is an exploded view of the jaw assembly of the shaft-and-jaw assembly of the forceps embodiment of FIG. 30.

In the embodiment of FIG. 30, end effector 640 takes the form of jaws (described in further detail in FIG. 37). In a preferred embodiment of the invention, frame 610 with collar 620, is fabricated from any suitable plastic or metal. Tube 630 is preferably fabricated from any suitable metal, such as stainless steel, and end effector 640 is likewise preferably fabricated from any suitable metal, such as stainless steel. Further, the components of handle assembly 700 are preferably fabricated from any suitable plastic or metal.

FIGS. 31-34 are perspective views of modular forceps 500 of FIG. 30, showing shaft-and-jaw assembly 600 in the process of removal from the handle assembly 700. Shaft-and-jaw assembly 500 may be held in position within handle assembly using any suitable means (not shown in this set of figures), such as friction fit, a snap fit, a cap, etc. For a specific contemplated retention mechanism, refer to FIGS. 39-43 and the corresponding text hereinafter. In order to separate shaft-and-jaw assembly 600 from handle assembly 700, an operator (not shown) may grasp forceps 500, by tube 630 and palm grip 710, and pivot shaft-and-jaws assembly 600 in the direction of arrow A.

Figure 35:
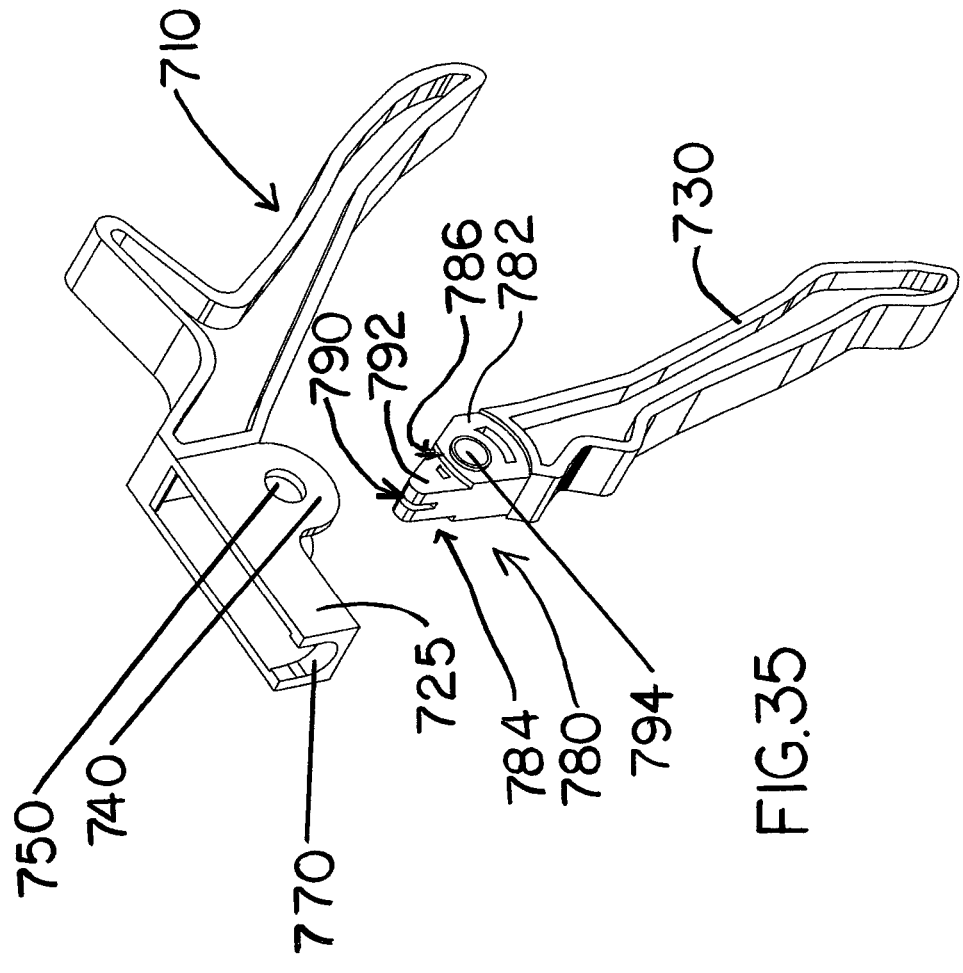
FIG. 35 is a perspective exploded view of the handle assembly of the forceps embodiment of FIG. 30.

FIG. 35 is a perspective exploded view of the handle assembly of the forceps embodiment of FIG. 30, showing further details of the components thereof. An upper end 780 of lever 730 is partitioned into a lower wider region 782 and an upper narrower region 784, demarcated by arcuate shoulders 786 on each side thereof. Upper region 784 is, in turn, divided at its upper end by a longitudinally-extending slit 790 into two lobes 792. A shallow cylindrical post 794 extends laterally outwardly from an outwardly-facing surface of each side of lower region 782. A corresponding pair of downwardly concave shoulders (not shown) may be provided on the opposing inside faces of ears 740, providing guide/bearing surface for shoulders 782, to provide controlled pivoting of lever 730 relative to palm grip 710. Ears 740 are provided with a limited amount of resiliency, to allow them to be spread apart, to facilitate insertion of upper end 780, and in particular, upper region 784 thereof, into the gap between ears 740. As posts 794 come into alignment with apertures 750, ears 740 will snap into place, holding lever 730 in position for pivotable movement relative to palm grip 710.

Figure 36:
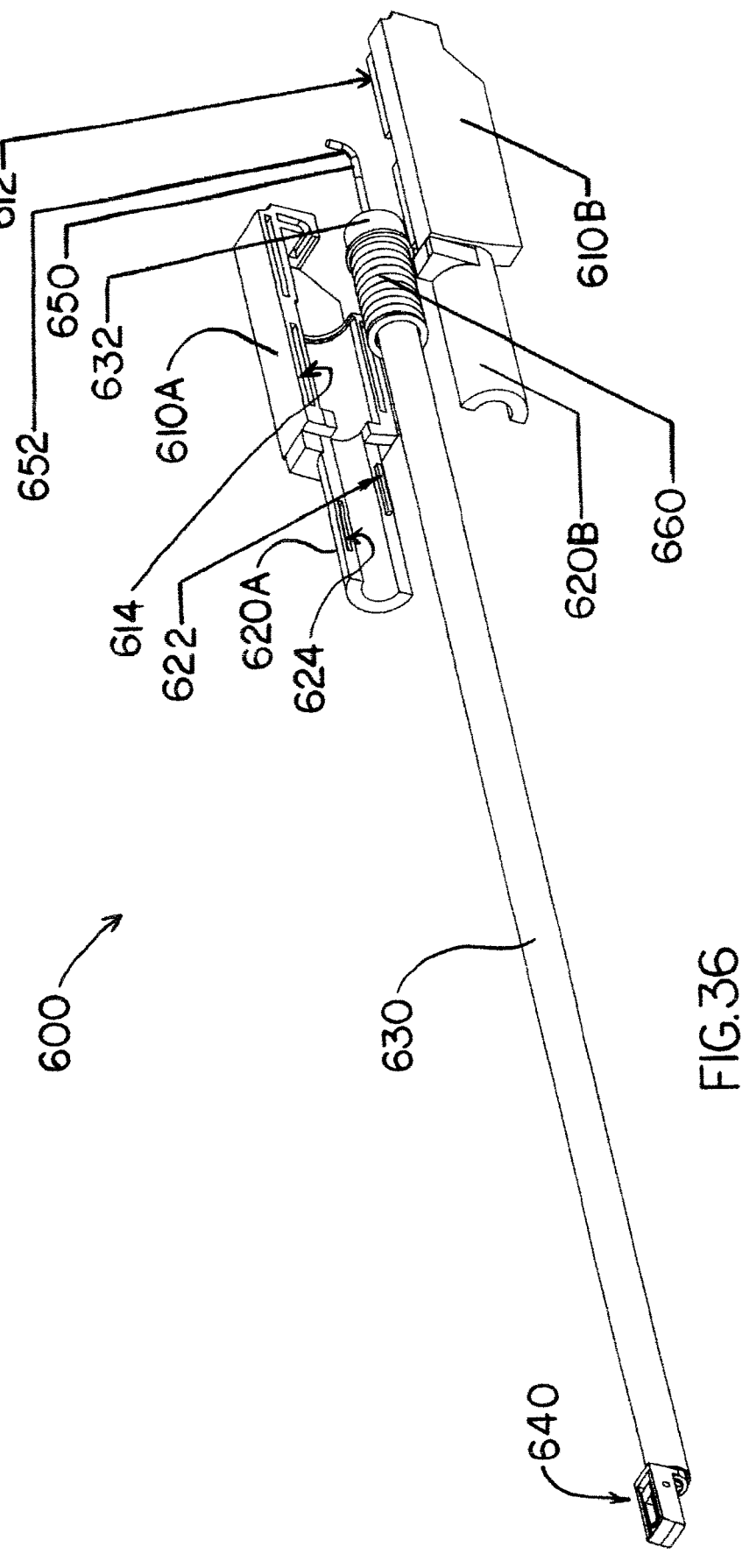
FIG. 36 is a partially exploded view of the shaft-and-jaw assembly of the forceps embodiment of FIG. 30.

FIG. 36 is a partially exploded view of the shaft-and-jaw assembly of the forceps embodiment of FIG. 30. In an embodiment of the invention, frame 610 with corresponding collar 620 is fabricated as frame and collar halves 610A/620A and 610B/620B, respectively. Frame half 610A is provided with slots 614, and collar half 620A is provided with tab 622 and slot 624, which are located, sized and shaped to mate with tabs 612 on half 620B, and a corresponding tab and slot (not shown) in collar half 620B. In embodiments of the invention, upon final assembly of shaft-and-jaw assembly 600, frame and collar halves 610A/620A and 610B/620B are affixed together using suitable means, such as adhesive, or sonic or thermal welding, or any suitable combination thereof.

Figure 38:
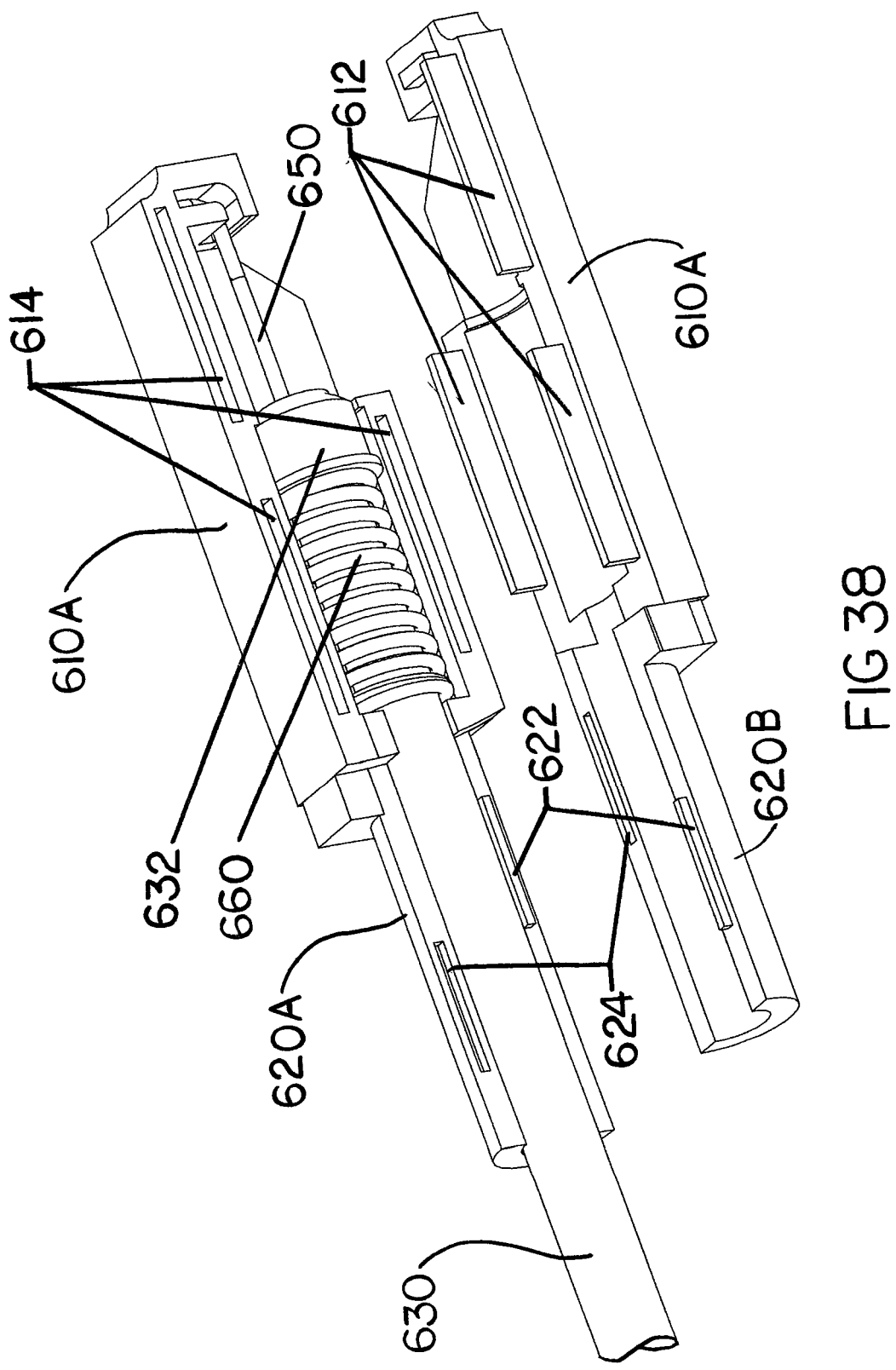
FIG. 38 is a further perspective exploded view of the proximal end of the shaft-and-jaw assembly of the forceps embodiment of FIG. 30.

Further, stop collar 632 is disposed on a proximal end of tube 630. An actuating member, in the form of rod 650 extends axially through the hollow interior of tube 630, beyond both ends of tube 630, and has hooked ends 652, 654 (FIG. 37), respectively. Coil spring 660 surrounds the proximal end of tube 630 and abuts stop collar 632. FIG. 38 illustrates proximal end of tube 630, with stop collar 632, coil spring 660 and rod 650 in position within frame half 610A.

FIG. 37 is an exploded view of the jaw assembly of the shaft-and-jaw assembly of the forceps embodiment of FIG. 30. Jaw assembly 640 includes fixed jaw 670 and pivoting jaw 680. Fixed jaw 670 comprises box 674 having through-holes 676 on opposite sidewalls thereof. Box 674 is attached, in a radially laterally displaced manner, to insert tube 672. On a distal front wall of box 674, a tooth or spike 678 projects upwardly. Pivoting jaw 680 comprises box 682, which may be monolithically formed, or built-up from a plurality of separate plate-like members. Box 674 further includes a distal front wall 684, with a lower edge 686, the degree of sharpness of which may vary, from specific implementation to another, depending upon the objective of the forceps, whether to cut or merely grip, tissue. Opposed lateral sidewalls of box 682 have openings 688, which may be merely holes, or which, in an embodiment in which the material between the sidewalls is solid, represent the openings at opposite ends of a single through-bore or passage. Arm 690 extends downwardly and rearwardly from box 682 and includes a through-hole 692. An outer perimeter of box 682 is sized to enable the insertion of box 682 into a central opening of box 674, so that openings/throughbore 688 align coaxially with through-holes 676, such that a pin or rivet (not shown) is passed therethrough, such that pivoting jaw 680 is enabled to pivot relative to fixed jaw 670. During assembly, rod 650 is passed through tube 630, and hook 654 is inserted into through-hole 692 and insert tube 672 is inserted into the distal end of tube 630, such that axial movement of rod 650 relative to tube 630 causes pivoting movement of pivoting jaw 680 relative to fixed jaw 670. It is to be noted that the rectangular "box" shape of jaw assembly 640 is merely an exemplary configuration, and other shapes, such as a pointed triangular shape, or an arcuate, circular, or elliptical planform may be adopted, as desired to meet the requirements of a particular procedure or use environment, without departing from the scope of the invention.

Assembly of modular forceps 500 is accomplished in the following manner. A fully assembled shaft-and-jaw assembly is grasped by a user (not shown), such that box frame 610 is held at an angle to slot 760, similar to the orientation illustrated in FIG. 33. As shaft-and-jaw assembly 600 is pushed into slot 760, a proximal end of rod 650, between hook 652 and collar stop 620, is received within slit 790 of lever 730. In a preferred embodiment of the invention, coil spring 660 is always under compression, so that it tends to push against collar stop 620 proximally toward palm grip 710, which, in turn, has the effect of pushing against upper region 784 of upper end 780, causing the lower free end of lever 730 to pivot away from the lower end of palm grip 710.

In an at-rest configuration, axially slidable tube 630 is in its rearwardmost position, relative to axially fixed rod 650. As such, rod 650 pushes forwardly on arm 690, pivoting pivotable jaw 680 to its open position. In use, when sufficient gripping pressure is exerted on lever 730 to overcome coil spring 660, lever upper end 780 moves distally, pushing shaft 630 in the distal direction, and in turn pushing box 674 of fixed jaw 670 in a distal direction. Because rod 650 is fixed against axial movement by hook 652 engaged with frame 610, the forward/distal movement of frame 674 causes arm 690 to be pivoted rearwardly, in turn causing pivoting jaw 680 to pivot downwardly to its closed configuration.

In an alternative embodiment, and similar to the embodiment of FIGS. 1-29, jaw assembly 640 is configured to be removably attached to the distal end of tube 630, to enable different configurations of jaws or other devices to be removably attached to tube 630 and rod 650. Any suitable connection means, such as a threaded connection, a snap-fit connection, a bayonet connection, etc., may be employed, provided the connection is sufficiently robust to prevent separation of the end effector from the tube during use or other normal handling.

FIGS. 39-42 illustrate a further alternative embodiment of the modular forceps of the present invention. Modular forceps 800 is, except as expressly described hereinafter, functionally, and structurally identical to the embodiment(s)

described with respect to FIGS. 30-38. Structures in FIGS. 39-43 that are analogous to similar structures in the embodiment of FIGS. 30-38, which have not been expressly called out or discussed, may be presumed to be identical, or substantially and functionally identical to those analogous corresponding structures in FIGS. 30-38.

Figure 39:
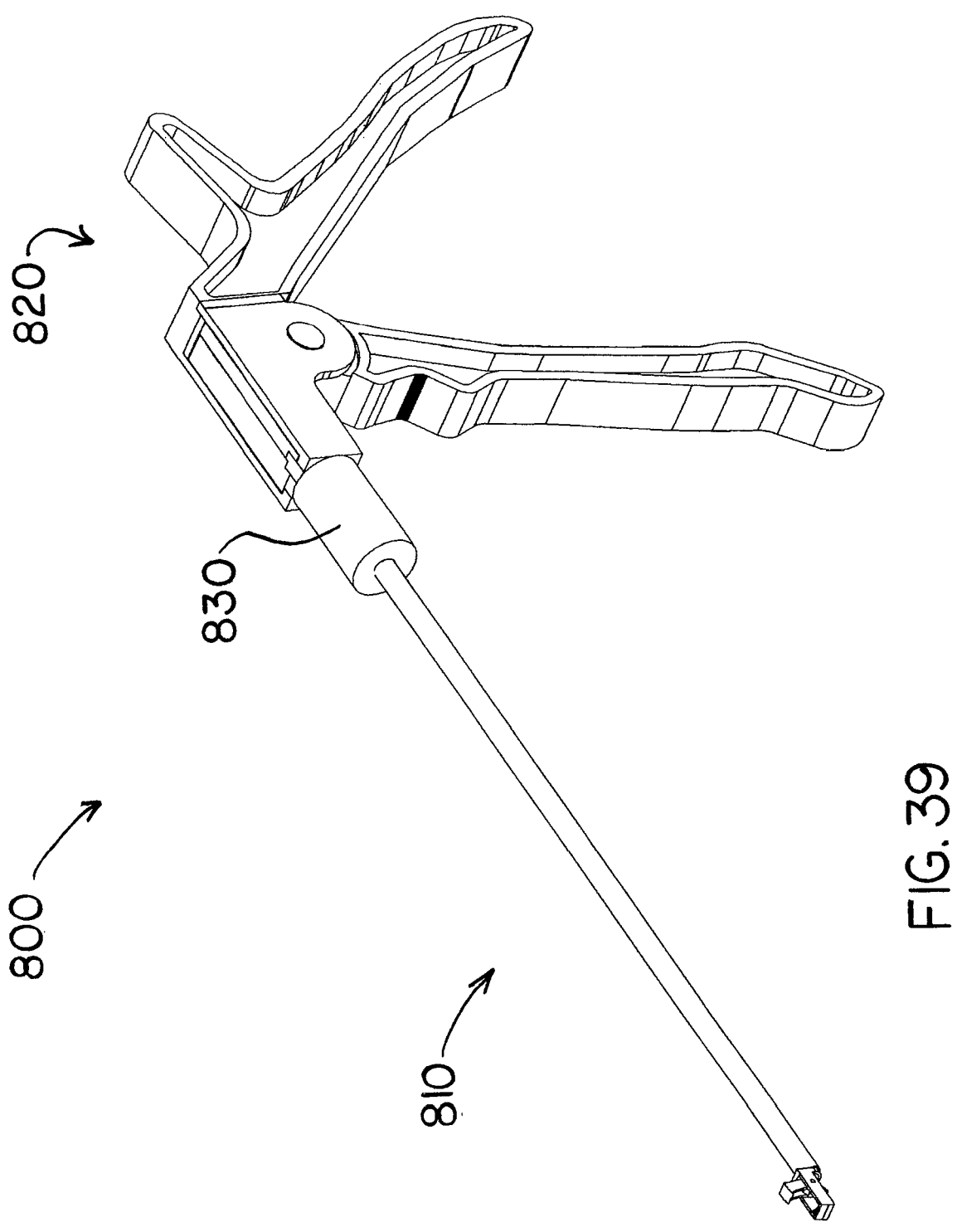
FIG. 39 is a perspective view of the modular forceps, in fully assembled configuration, according to another embodiment of the invention.

FIG. 39 is a perspective view of modular forceps 800, in fully assembled configuration, according to another embodiment of the invention. Forceps 800 includes shaft-and-jaws assembly 810 and handle assembly 820. Forceps 800 additionally includes assembly lock 830.

Figure 40:
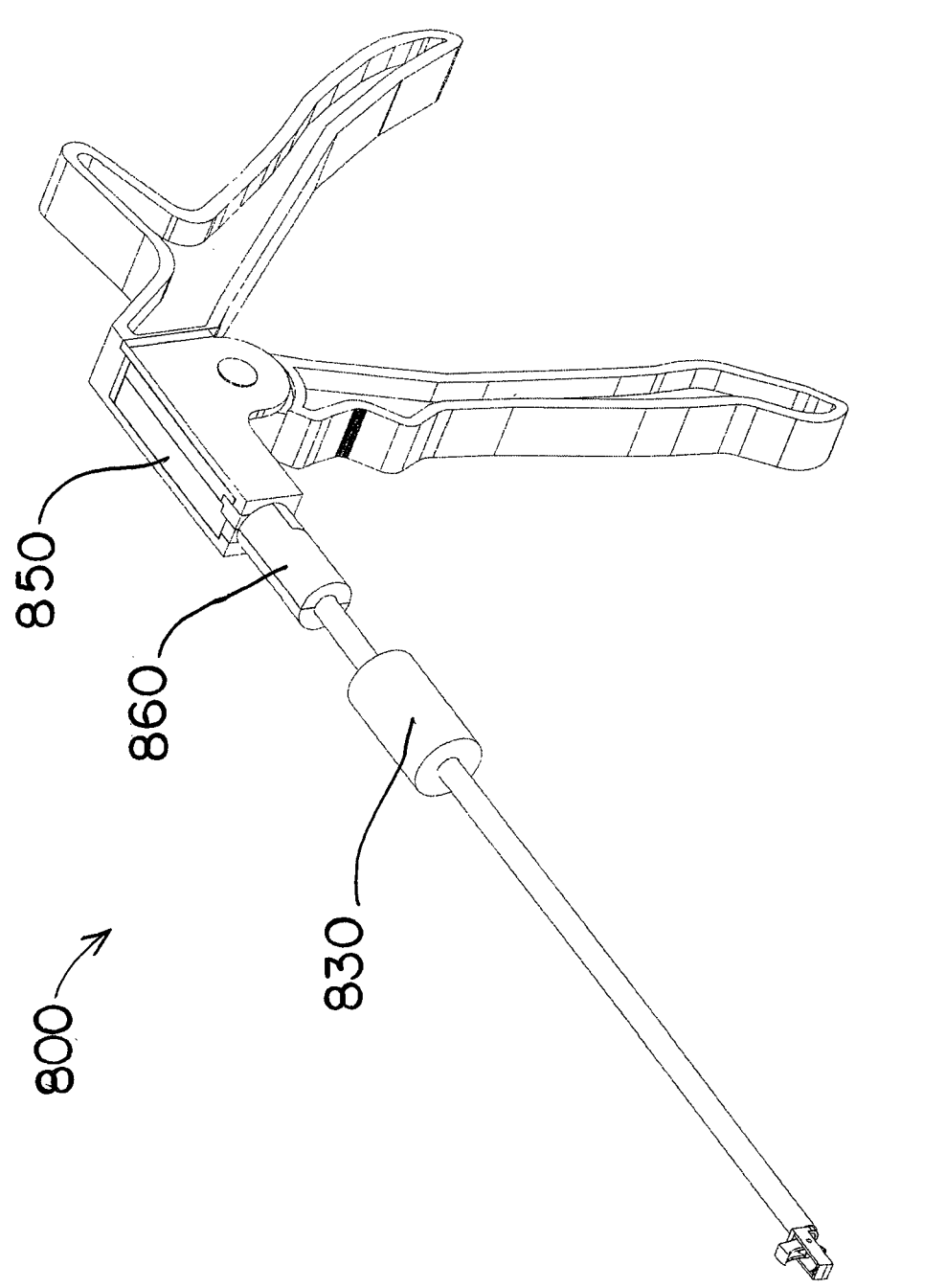
FIG. 40 is a perspective view of the modular forceps according to the embodiment of FIG. 39, partially disassembled.

FIG. 40 is a perspective view of modular forceps 800, according to the embodiment of FIG. 39, partially disassembled. Assembly lock 830 engages, e.g., via internal threading (not shown) to a correspondingly-threaded (not shown) outer surface of collar 860, which extends from frame 850.

Figure 41:
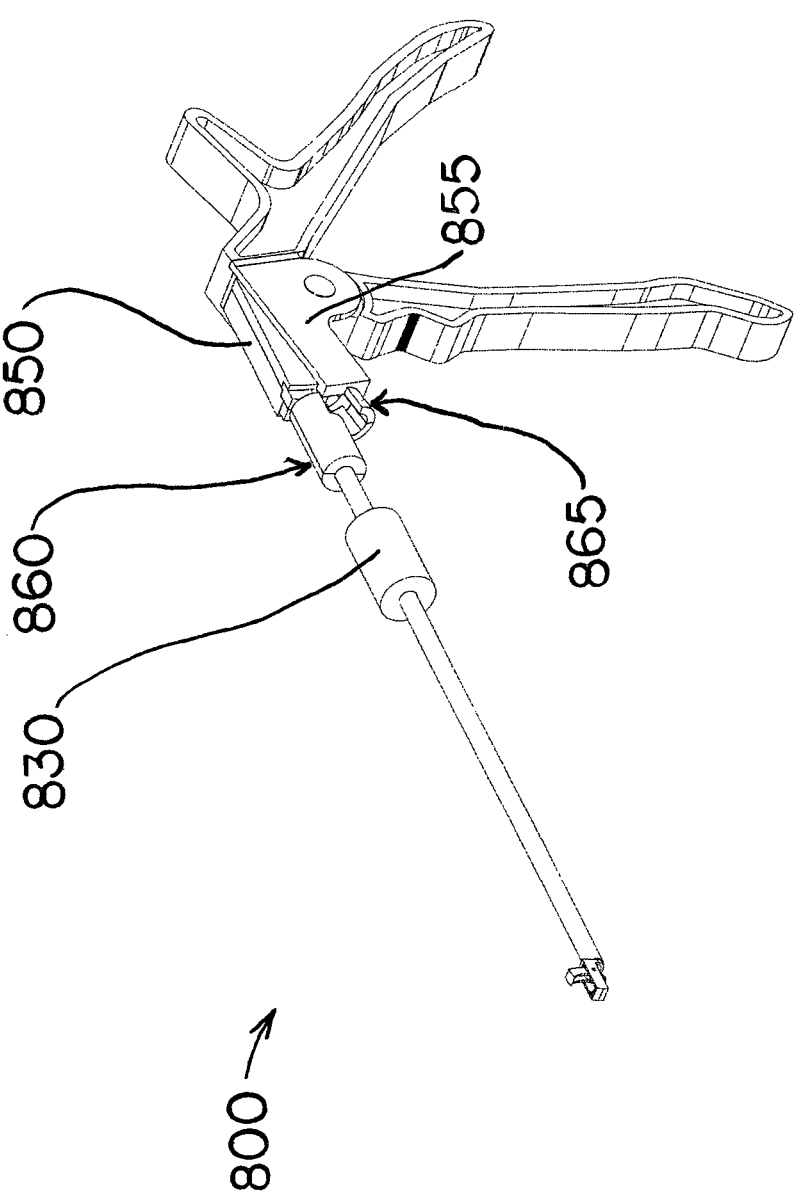
FIG. 41 is a perspective view of the modular forceps according to the embodiment of FIG. 39, at a still further stage in the disassembly process.

FIG. 41 is a perspective view of modular forceps 800, according to the embodiment of FIG. 39, at a still further stage in the disassembly process. In this embodiment, receiver 855 of handle assembly 820 includes a projection 865, which mates with a corresponding notch or recess 870 (FIG. 42) formed in the underside of collar 860. Threads (not shown) may also be formed on the outer surface of projection 865 to engage with the internal threading on assembly lock 830. In an alternative confirmation, the exterior of collar 860 and the interior of assembly lock 830 may be smooth, with their interengagement simply being one of a forced, interference or friction fit.

Figure 42:
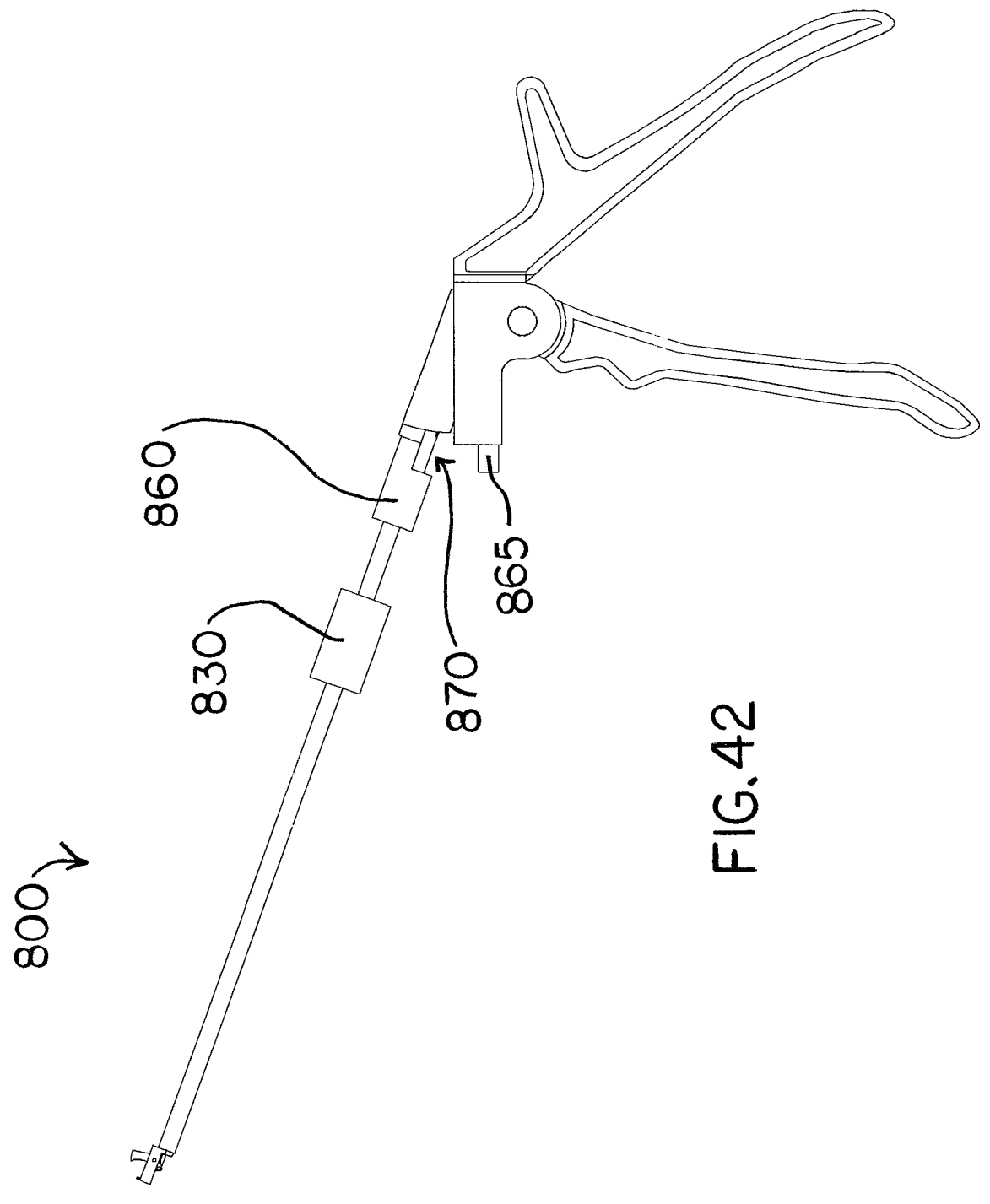
FIG. 42 is a side elevation of the modular forceps according to the embodiment of FIG. 39, at yet a still further stage of disassembly.

FIG. 42 is a side elevation of the modular forceps according to the embodiment of FIG. 39, at yet a still further stage of disassembly.

Figure 43:
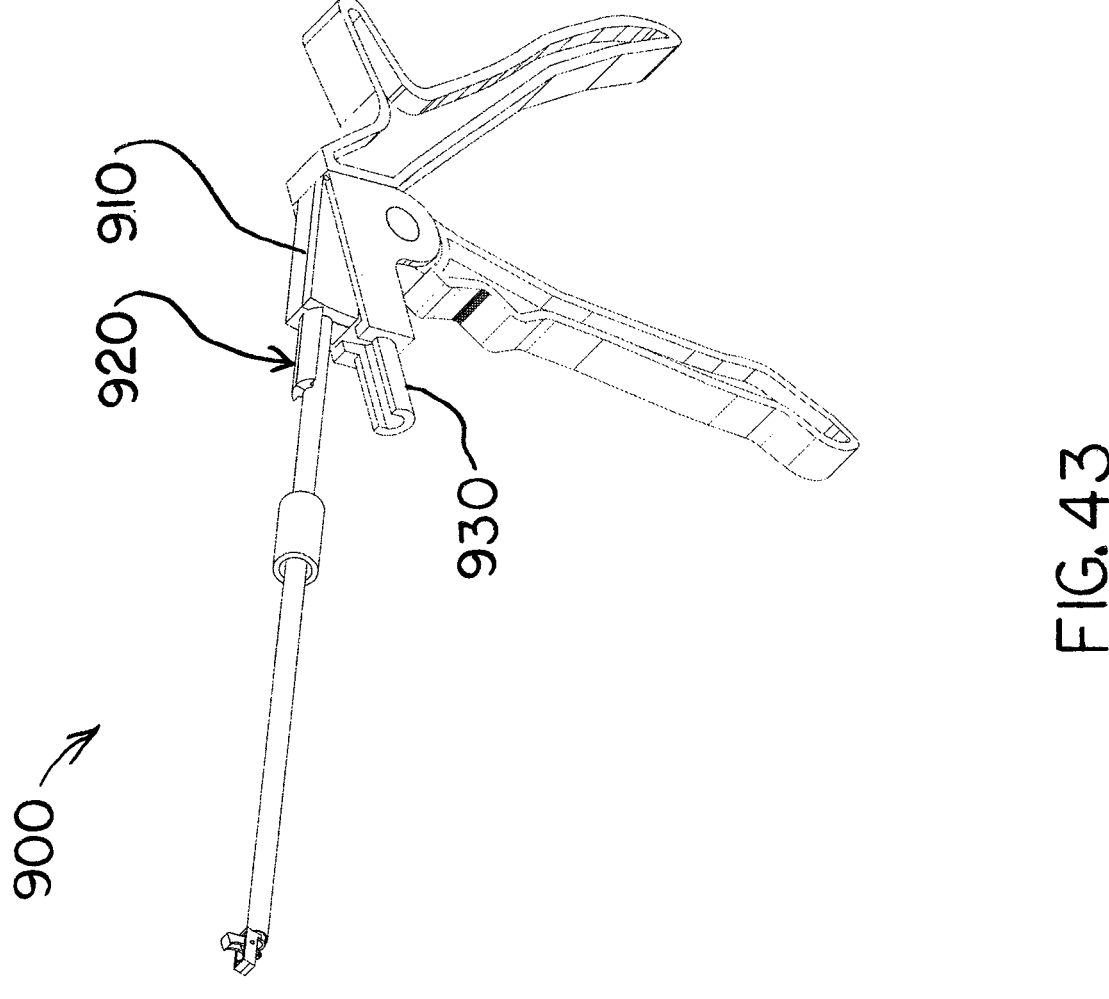
FIG. 43 is a perspective view of another alternative embodiment of the modular forceps, similar to the embodiment of FIGS. 39-42.

FIG. 43 is a perspective view of a further alternative embodiment. Forceps 900 is, except as expressly described hereinafter, functionally, and structurally identical to the embodiment(s) described with respect to FIGS. 39-42. Structures in FIGS. 43-44, that are analogous to similar structures in the embodiment of FIGS. 39-42, which have not been expressly called out or discussed, may be presumed to be identical, or substantially and functionally identical to those analogous corresponding structures in FIGS. 39-42.

Figure 44:
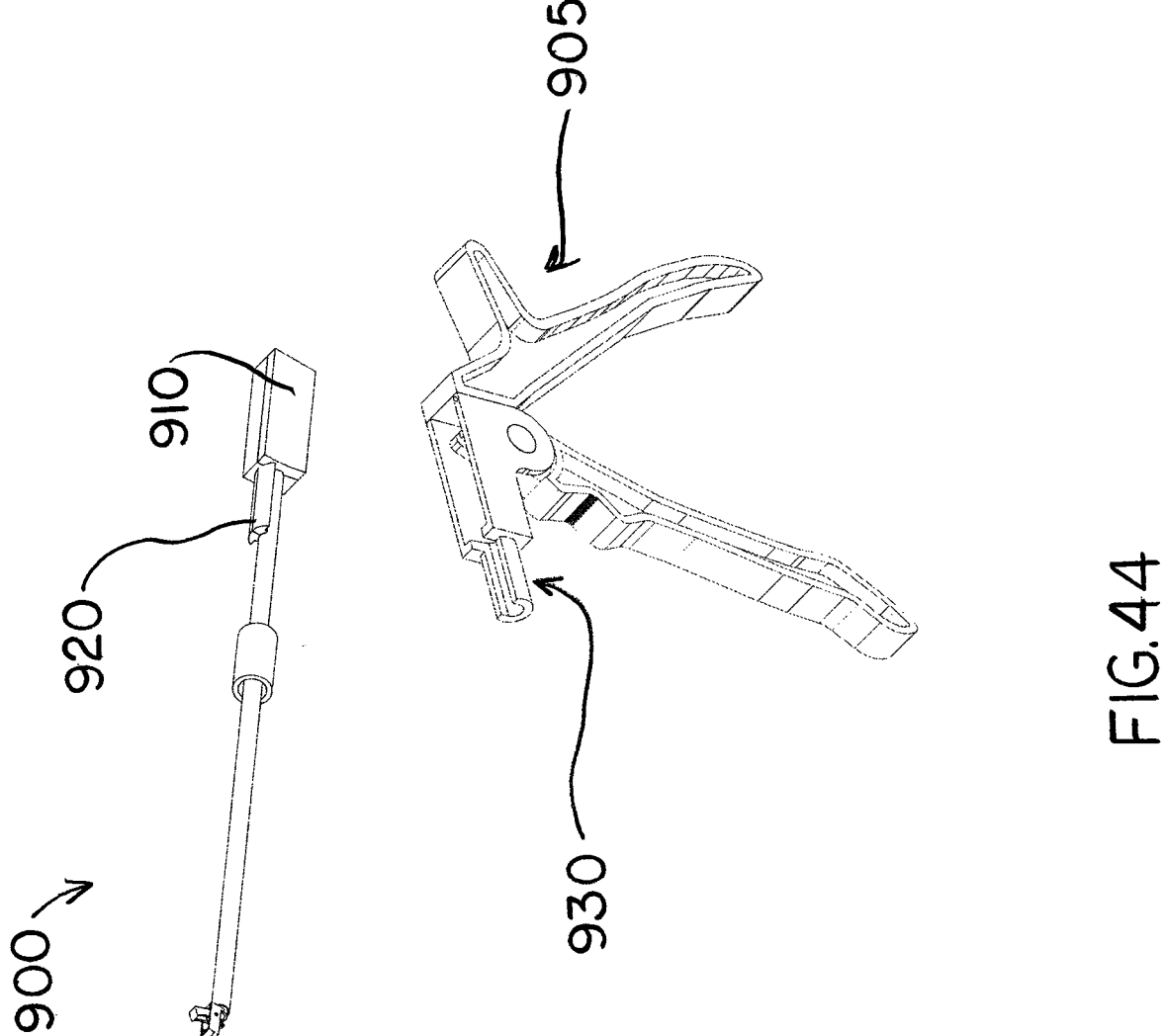
FIG. 44 is a perspective view of the embodiment of FIG. 43, shown completely disassembled.

In the embodiment of FIGS. 43-44, the collar structure of the shaft-and-jaws assembly is partitioned, such that an upper half, more or less, of the collar remains as collar sector 920, extending from frame 910. A remaining portion of the collar is formed as semi-tubular extension 930, from the receiver of handle assembly 905. Collar sector 920 and extension 930 are provided with external threading, to engage with the assembly lock, in a similar manner to the embodiment of FIGS. 39-42. In an alternative embodiment, these surfaces may be smooth, such that a forced, interference or friction fit is used to maintain the assembly lock in place.

The present disclosure further contemplates and includes a system, wherein at least a single handle assembly is provided and a plurality of shaft-and-jaw assemblies are provided with the handle assembly, wherein the shaft-and-jaw assemblies include one or more of a plurality of identical shaft-and-jaw assemblies having identical end effectors, a plurality of shaft-and-jaw assemblies having at least two different configurations of end effectors, a plurality of shaft-and-jaw assemblies, wherein at least one shaft-and-jaw assembly is structured to permit removal and replacement of the end effectors, with a plurality of duplicate and/or different end effectors are provided.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

Although the invention has been described with reference to the above examples, it will be understood that many modifications and variations are contemplated within the true spirit and scope of the embodiments of the invention as disclosed herein. Many modifications and other embodiments of the invention set forth herein will come to mind to one skilled in the art to which the invention pertains having the benefit of the teachings presented in the foregoing descriptions and the associated drawings. Therefore, it is to be understood that the invention shall not be limited to the specific embodiments disclosed and that modifications and other embodiments are intended and contemplated to be included within the scope of the appended claims. Although specific terms are employed herein, they are used in a generic and descriptive sense only and not for purposes of limitation.

The invention claimed is:

1. A modular forceps, comprising:
a handle assembly, including
a palm grip,
a receiver fixedly coupled to the palm grip, and
a lever, pivotably coupled to the receiver and distally positioned relative to the palm grip, the receiver defining an upwardly open slot and a distal end opening; and
a shaft-and-jaw assembly releasably couplable to the handle assembly, the shaft-and-jaw assembly including
a frame having a cavity therein,
an elongated hollow tube extending distally from a forward end of the frame, the hollow tube having opposed proximal and distal open ends, the hollow tube in communication with the cavity, the tube slidably received within the frame,
a jaw assembly disposed on the distal end of the hollow tube, the jaw assembly including at least a pivotable jaw pivotably mounted to the distal end of the hollow tube, and
an actuation member fixedly coupled to the frame and the pivotable jaw, the tube axially movable relative to the actuation member, and an end of the lever engageable with a proximal end of the tube, such that pivoting movement of the lever toward the palm grip causes the lever to exert a pushing force on the tube, causing the distal end of the tube to, in turn, pivot the pivotable jaw from an open position to a closed position, and further comprising an assembly lock mechanism, comprising:
a receiver collar portion extending distally from a front region of the receiver;
a frame collar portion extending distally from a front region of the frame, the receiver and frame collar portions at least partially mating to form a complete collar encircling a proximal portion of the hollow tube, the receiver and frame collar portions having on an external surface thereof, threaded sections that, upon mating of the receiver and frame portions, forms an at least substantially continuous external thread; and
an assembly lock cylinder, through which the hollow tube is inserted, the assembly lock cylinder having internal threading therein, such that upon insertion of the shaft-and-jaw assembly into the receiver, the assembly lock cylinder may be reversibly and removably screwed onto the receiver and frame collar portions to maintain the shaft-and-jaw assembly securely in position in the handle assembly during use.

2. A modular forceps, comprising:
a handle assembly, including
a palm grip,
a receiver fixedly coupled to the palm grip, and
a lever, pivotably coupled to the receiver and distally positioned relative to the palm grip, the receiver defining an upwardly open slot and a distal end opening; and
a shaft-and-jaw assembly releasably couplable to the handle assembly, the shaft-and-jaw assembly including
a frame having a cavity therein,
an elongated hollow tube extending distally from a forward end of the frame, the hollow tube having opposed proximal and distal open ends, the hollow tube in communication with the cavity, the tube slidably received within the frame,
a jaw assembly disposed on the distal end of the hollow tube, the jaw assembly including at least a pivotable jaw pivotably mounted to the distal end of the hollow tube, and
an actuation member fixedly coupled to the frame and the pivotable jaw, the tube axially movable relative to the actuation member, and an end of the lever engageable with a proximal end of the tube, such that pivoting movement of the lever toward the palm grip causes the lever to exert a pushing force on the tube, causing the distal end of the tube to, in turn, pivot the pivotable jaw from an open position to a closed position, and further comprising an assembly lock mechanism, comprising:
a receiver collar portion extending distally from a front region of the receiver;
a frame collar portion extending distally from a front region of the frame, the receiver and frame collar portions at least partially mating to form a complete collar encircling a proximal portion of the hollow tube,
the receiver and frame collar portions defining collectively, a substantially smooth external surface; and
an assembly lock cylinder, through which the hollow tube is inserted, the assembly lock cylinder having a substantially smooth internal surface, the respective smooth internal and external surfaces interfacing with a forced frictional or interference fit, when the assembly lock cylinder is pushed onto the collar, to maintain the shaft-and-jaw assembly securely in position in the handle assembly during use.

* * * * *